United States Patent
Assmann et al.

(10) Patent No.: US 7,211,436 B1
(45) Date of Patent: May 1, 2007

(54) COMPOSITIONS AND METHODS FOR REGULATING ABSCISIC ACID-INDUCED CLOSURE OF PLANT STOMATA

(75) Inventors: Sarah M. Assmann, State College, PA (US); Jiaxu Li, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 605 days.

(21) Appl. No.: 09/606,736

(22) Filed: Jun. 29, 2000

Related U.S. Application Data

(60) Provisional application No. 60/192,499, filed on Mar. 28, 2000, provisional application No. 60/176,245, filed on Jan. 14, 2000, provisional application No. 60/142,039, filed on Jul. 1, 1999.

(51) Int. Cl.
- *C12Q 1/68* (2006.01)
- *C12N 15/00* (2006.01)
- *C12N 15/83* (2006.01)
- *C07H 21/02* (2006.01)
- *C07H 21/04* (2006.01)

(52) U.S. Cl. .......... 435/468; 435/6; 435/91.1; 435/320.1; 435/375; 435/419; 536/23.1; 536/23.2; 536/23.6; 536/24.3

(58) Field of Classification Search ............ 435/6, 435/91.1, 91.5, 468, 320.1, 410, 419, 375; 536/23.1, 23.2, 23.6, 24.3, 24.33, 24.5
See application file for complete search history.

(56) References Cited

FOREIGN PATENT DOCUMENTS

WO WO 95/05731 3/1995

OTHER PUBLICATIONS

Gallois, P., Apr. 27, 1993, Genbank Accession, No. L05561.*
Gallois, P., Apr. 27, 1993, Genbank Accession, No. L05562.*
Anderberg, R.J. anad Walker-Simmons, M.K. Isolation of a Wheat cDNA Clone for an Abscisic Acid-Inducible Transcript with Homology to Protein Kinases. *Proc. Natl. Acad. Sci.*. 1992. 89:10183-10187. Plant Biology. USA.
Baur, B., Fischer, K., Winter, Klaus, and Dietz, K-J cDNA Sequence of a Protein Kinase from the Inducible Crassulacean Acid Metabolism Plant *Mesembryanthemum Crystallinum* L., Encoding a SNF-1 Homology. *Plant Physiol.*. 1994. 106:1225-1226. USA.
Hotta, H., Aoki, N., Matsuda, T. and Adachi, T. Molecular Analysis of a Novel Protein Kinase in Maturing Rice Seed. *Gene*. 1998. 213:47-54.
Koornneef, M., Jorna, M.L., Brinkhorst-van der Swan, D.L.C. and Karssen, C.M. The Isolation of Abscisic acid (ABA) Deficient Mutants by Selection of Induced Revertants in Non-Germinating Gibberellin Sensitive Lines of *Arabidopsis Thaliana* (L.) He6ynh. *Theor. Appl. Genet.* 1982. 61:385-393. USA.
Koornneef, M., Rueling, G. and Karssen, C.M. The Isolation and Characterization of Abscisic Acid-Insensitive Mutants of *Arabidopsis Thaliana*. *Physiol Plant*. 1984. 61:377-383 USA.
Lee, S.H., Lee, M.H., Chung, W.I. and Liu, J.R. *WAPK*, A Ser/Thr Protein Kinase gene of *Nicotiana Tabacum*, is Uniquely Regulated by Wounding, Abscisic Acid and Methyl Jasmonate. *Mol. Gen. Genet.* 1998.
Leung, J., Bouvier-Durand, M., Morris, P-C., Guerrier, D., Chefdor, F. and Giraudat, J. *Arabidopsis* ABA Response Gene ABI1: Features of a Calcium-Modulated Protein Phosphatase. *Science*. 1994. 264:1448-1455. USA.
Li, J. and Assmann, S.M. An Abscisic Acid Activated and Calcium-Independent Protein Kinase from Guard Cells of Fava Bean. *The Plant Cell*. 1996. 8:2359-2368. American Society of Plant Physiologists. USA.
Mori, I.C. and Muto, S. Abscisic Acid Activates a 48-Kilodalton Protein Kinase in Guard Cell Protoplasts *Plant Physiol*. 1997. 113:833-839. USA.
Yoon, H.W., Kim, M.C., Shin, P.G., Kim, J.S., Kim, C.Y., Lee, S.Y., Hwang, I., Bahk, J.D., Hong, J.C., Han, C. and Cho, M.J. Differential Expression of Two Functional Serine/Threonine Protein Kinases from Soyabean that have an Unusual Acidic Domain at the Carboxy Terminus. *Mol Gen Genet*. 1997. 255:359-371. USA.
Li, J. et al., Guard Cells Possess a Calcium-Dependent Protein Kinase That Phosphorylates the KAT1 Potassium Channel. Plant Physiol. 116:785-795 (1998).

* cited by examiner

*Primary Examiner*—Jane Zara
(74) *Attorney, Agent, or Firm*—Woodcock Washburn LLP

(57) ABSTRACT

A novel gene, AAPK, is disclosed. Loss of function of the protein encoded by AAPK is associated with reduced sensitivity to abscisic acid-induced stomatal closure in plants. Also disclosed are transgenic plants and mutants having altered sensitivity to abscisic acid-mediated transpiration and other desirable agronomic features. The regulation of transpiration provided by the present invention is different from that of previously described mechanisms to control transpiration in plants.

10 Claims, 4 Drawing Sheets

```
Query:   3   MPPPIMHDSDRYDFVRDIGSGNFGVARLMTDKLTKDLVAVKYIERGDKIDENVKREIINH  62
             M  PIMHDSDRY+ V+DIGSGNFGVARLM DK + +LVAVKYIERG+KIDENVKREIINH
Sbjct:  10   MDLPIMHDSDRYELVKDIGSGNFGVARLMRDKQSNELVAVKYIERGEKIDENVKREIINH  69

Query:  63   RSLRHPNIVRFKEVILTPTHLAIVMEYASGGEMSDRISKAGRFTEDEARFFFQQLISGVS 122
             RSLRHPNIVRFKEVILTPTHLAIVMEYASGGE+ +RI  AGRF+EDEARFFFQQLISGVS
Sbjct:  70   RSLRHPNIVRFKEVILTPTHLAIVMEYASGGELFERICNAGRFSEDEARFFFQQLISGVS 129

Query: 123   YCHSMQVCHRDLKLENTLLDGDPALHLKICDFGYSKSSVLHSQPKSTVGTPAYIAPEVLL 182
             YCH+MQVCHRDLKLENTLLDG PA  LKICDFGYSKSSVLHSQPKSTVGTPAYIAPEVLL
Sbjct: 130   YCHAMQVCHRDLKLENTLLDGSPAPRLKICDFGYSKSSVLHSQPKSTVGTPAYIAPEVLL 189

Query: 183   KQEYDGKIADVWSCGVTLYVMLVGSYPFEDPDNPKDFRKTIQRVLSVQYSVPDFVQISPE 242
             K+EYDGK+ADVWSCGVTLYVMLVG+YPFEDP+ PK+FRKTI R+L+VQY++PD+V ISPE
Sbjct: 190   KKEYDGKVADVWSCGVTLYVMLVGAYPFEDPEEPKNFRKTIHRILNVQYAIPDYVHISPE 249

Query: 243   CRDIISRIFVFDPAERITIPEIMKNEWFRKNLPADLVNENIMDNQFEEPDQPMQSMDTIM 302
             CR +ISRIFV DPA+RI+IPEI  +EWF KNLPADL+N+N M  QF+E DQP QS++ IM
Sbjct: 250   CRHLISRIFVADPAKRISIPEIRNHEWFLKNLPADLMNDNTMTTQFDESDQPGQSIEEIM 309

Query: 303   QIISEATVPAAGSYYFDEFIEVDEDMDEIDSDY-ELDVDSSGEIVYAI 349
             QII+EATVP AG+  + ++ D+ ++++SD +LD+DSSGEIVYA+
Sbjct: 310   QIIAEATVPPAGTQNLNHYLTDDDMEEDLESDLDDLDIDSSGEIVYAM 357
```

Figure 3

```
Query:   1   MDMPPPIMHDSDRYDFVRDIGSGNFGVARLMTDKLTKDLVAVKYIERGDKIDENVKREII  60
             M +  PIMHDSDRYDFV+DIGSGNFGVARLMTD++TK+LVAVKYIERG+KIDENV+REII
Sbjct:  10   MPIDLPIMHDSDRYDFVKDIGSGNFGVARLMTDRVTKELVAVKYIERGEKIDENVQREII  69

Query:  61   NHRSLRHPNIVRFKEVILTPTHLAIVMEYASGGEMSDRISKAGRFTEDEARFFFQQLISG 120
             NHRSLRHPNIVRFKEVILTP+HLAIVMEYA+GGE+ +RI  AGRF+EDEARFFFQQLISG
Sbjct:  70   NHRSLRHPNIVRFKEVILTPSHLAIVMEYAAGGELYERICNAGRFSEDEARFFFQQLISG 129

Query: 121   VSYCHSMQVCHRDLKLENTLLDGDPALHLKICDFGYSKSSVLHSQPKSTVGTPAYIAPEV 180
             VSYCH+MQ+CHRDLKLENTLLDG PA   LKICDFGYSKSSVLHSQPKSTVGTPAYIAPE+
Sbjct: 130   VSYCHAMQICHRDLKLENTLLDGSPAPRLKICDFGYSKSSVLHSQPKSTVGTPAYIAPEI 189

Query: 181   LLKQEYDGKIADVWSCGVTLYVMLVGSYPFEDPDNPKDFRKTIQRVLSVQYSVPDFVQIS 240
             LL+QEYDGK+ADVWSCGVTLYVMLVG+YPFEDP   P+D+RKTIQR+LSV YS+P+ + +S
Sbjct: 190   LLRQEYDGKLADVWSCGVTLYVMLVGAYPFEDPQEPRDYRKTIQRILSVTYSIPEDLHLS 249

Query: 241   PECRDIISRIFVFDPAERITIPEIMKNEWFRKNLPADLVNENIMDNQFEEPDQPMQSMDT 300
             PECR +ISRIFV DPA RITIPEI  ++WF KNLP DL++EN M +QF+EP+QPMQS+DT
Sbjct: 250   PECRHLISRIFVADPATRITIPEITSDKWFLKNLPGDLMDENRMGSQFQEPEQPMQSLDT 309

Query: 301   IMQIISEATVPAAGSYYFDEF----IEVDEDMDEIDSDYELDVDSSGEIVYAI 349
             IMQIISEAT+P   + D+F   +++D+DMD+ DS+ E+DVDSSGEIVYA+
Sbjct: 310   IMQIISEATIPTVRNRCLDDFMADNLDLDDDMDDFDSESEIDVDSSGEIVYAL 362
```

Figure 4

```
Query:    1  MDMPPPIMHDSDRYDFVRDIGSGNFGVARLMTDKLTKDLVAVKYIERGDKIDENVKREII  60
             M +  PIMHDSDRYDFV+DIGSGNFGVARLMTD++TK+LVAVKYIERG+KIDENV+REII
Sbjct:   10  MPIDLPIMHDSDRYDFVKDIGSGNFGVARLMTDRVTKELVAVKYIERGEKIDENVQREII  69

Query:   61  NHRSLRHPNIVRFKEVILTPTHLAIVMEYASGGEMSDRISKAGRFTEDEARFFFQQLISG  120
             NHRSLRHPNIVRFKEVILTP+HLAIVMEYA+GGE+ +RI  AGRF+EDEARFFFQQLISG
Sbjct:   70  NHRSLRHPNIVRFKEVILTPSHLAIVMEYAAGGELYERICNAGRFSEDEARFFFQQLISG  129

Query:  121  VSYCHSMQVCHRDLKLENTLLDGDPALHLKICDFGYSKSSVLHSQPKSTVGTPAYIAPEV  180
             VSYCH+MQ+CHRDLKLENTLLDG PA   LKICDFGYSKSSVLHSQPKSTVGTPAYIAPE+
Sbjct:  130  VSYCHAMQICHRDLKLENTLLDGSPAPRLKICDFGYSKSSVLHSQPKSTVGTPAYIAPEI  189

Query:  181  LLKQEYDGKIADVWSCGVTLYVMLVGSYPFEDPDNPKDFRKTIQRVLSVQYSVPDFVQIS  240
             LL+QEYDGK+ADVWSCGVTLYVMLVG+YPFEDP   P+D+RKTIQR+LSV YS+P+ + +S
Sbjct:  190  LLRQEYDGKLADVWSCGVTLYVMLVGAYPFEDPQEPRDYRKTIQRILSVTYSIPEDLHLS  249

Query:  241  PECRDIISRIFVFDPAERITIPEIMKNEWFRKNLPADLVNENIMDNQFEEPDQPMQSMDT  300
             PECR +ISRIFV DPA RITIPEI ++WF KNLP DL++EN M +QF+EP+QPMQS+DT
Sbjct:  250  PECRHLISRIFVADPATRITIPEITSDKWFLKNLPGDLMDENRMGSQFQEPEQPMQSLDT  309

Query:  301  IMQIISEATVPAAGSYYFDEF----IEVDEDMDEIDSDYELDVDSSGEIVYAI  349
             IMQIISEAT+P   +  D+F   +++D+DMD+ DS+ E+DVDSSGEIVYA+
Sbjct:  310  IMQIISEATIPTVRNRCLDDFMADNLDLDDDMDDFDSESEIDVDSSGEIVYAL  362
```

COMPOSITIONS AND METHODS FOR REGULATING ABSCISIC ACID-INDUCED CLOSURE OF PLANT STOMATA

This application claims priority to U.S. Provisional Application Nos. 60/142,039, filed Jul. 1, 1999, 60/176,245, filed Jan. 14, 2000 and 60/192,499, filed Mar. 28, 2000, the entireties of which are incorporated by reference herein.

Pursuant to 35 U.S.C. §202(c), it is acknowledged that the U.S. Government has certain rights in the invention described herein, which was made in part with funds from the National Science Foundation, Grant Nos. MCB-9316319 and MCB-9874438.

FIELD OF THE INVENTION

The present invention relates to the field of molecular biology of plants. More specifically, it relates to the regulation of gas exchange and transpirational water loss in plants possessing stomata.

BACKGROUND OF THE INVENTION

Various scientific and scholarly articles are referred to throughout the specification. These articles are incorporated by reference herein to describe the state of the art to which this invention pertains.

In terrestrial plants, water is transported, from the roots to the leaves, down a water potential gradient from the soil to the air. Transpiration, or loss of water from the leaves, helps create lowered osmotic potential in the leaves, effectively drawing water from the xylem to the mesophyll cells into the air spaces in the leaves. Estimates are that 90% or more of the water taken up by plants is lost to the air via transpiration.

Transpirational loss of water by evaporation occurs mainly through the pores, called stomata, primarily located in the lower epidermis of the leaves. Each stoma is surrounded by two guard cells, which control the opening and closure of the stomata by their relative turgor pressure. The cell wall properties of guard cells allow them to deform such that when the guard cells develop turgor pressure, the stoma is opened, but when the guard cells lose turgor, the stoma closes.

The rate of evaporation of water from the air spaces of the leaf to the outside air depends on the water potential gradient between the leaf and the outside air. Environmental factors which directly influence the aperture of the plant's stomata affect its transpiration rate. Such factors include light conditions, relative humidity of the air, temperature, water status of the plant, $CO_2$ concentration, relative concentration of certain ions, and concentration of abscisic acid (ABA).

Abscisic acid is a multifunctional phytohormone involved in a variety of important protective functions including bud dormancy, seed dormancy and/or maturation, abscission of leaves and fruits, and response to a wide variety of biological stressors (e.g. cold, heat, salinity, and drought). It is also responsible for regulating stomatal closure by a mechanism independent of $CO_2$ concentration.

ABA is synthesized rapidly in response to water stress in plants, and is stored in the guard cells. During drought, ABA alteration of guard cell ion transport promotes stomatal closure and also prevents stomatal opening, thus reducing transpirational water loss. At the biochemical level, it is believed that the hormone sets off a variety of biological messages that require or include a protein phopsphorylation cascade. One member of this cascade was identified in guard cells of *Vicia faba* as an ABA-activated, calcium-independent protein kinase. (Li & Assmann, Plant Cell 8: 2359–2368, 1996; Mori & Muto, Plant Physiol. 113: 833–839, 1997). The kinase was identified by SDS polyacrylamide gel electrophoresis as a 48 kDa protein, but was not further isolated or characterized. It exhibited ABA-activated autophosphorylation and kinase activity.

Stomata simultaneously regulate both the transpiration of water and the exchange of gases for photosynthesis. Open stomata allow for maximum gas exchange rate so that photosynthetic reactions may proceed more quickly, however under these conditions, water loss will be maximal. On the other hand, closed stomata minimize transpirational water loss but also substantially reduce photosynthetic reaction rates. Paradoxically, the plant undergoes a continual trade-off between maximizing $CO_2$ uptake for carbon fixation, and minimizing desiccating water loss. Thus, the ability to control stomatal opening and closure could be of tremendous agronomic significance.

Several studies in the literature provide examples of the benefits of selecting for increased stomatal conductance under certain conditions. One system that has been studied extensively comprises eight lines of Pima cotton (*Gossypium barbadense*) obtained over 40 years of selection and showing a 3-fold range in yield. These and additional studies have confirmed the association of higher conductance with higher yield, and its genetic basis, in both Pima and Upland (*Gossypium hirsutum*) cotton. A similar correlation of increased yield, increased stomatal conductance, and decreased canopy temperatures has also been observed in a historical series of bread wheat cultivars. Taken collectively, this body or research suggests that selection or genetic engineering of plants to achieve increased stomatal conductance may be of widespread utility for crop plants grown under irrigation under supra-optimal temperatures.

The plant hormone abscisic acid (ABA) causes stomatal closure during periods of reduced water availability by reducing the ion and water content of the pair of guard cells that flanks each stoma. However, even when plants are well-watered, ABA still limits stomatal aperture, as shown by the fact that mutants of tomato and *Arabidopsis* that are deficient in either ABA-production or ABA-sensing have larger stomatal apertures than wild-type plants, even when water is plentiful. In other words, the ABA response is protective; always somewhat limiting to water loss, but thus unavoidably, also limiting to $CO_2$ uptake. This ABA-mediated limitation of water loss is of no benefit however, to the grower who irrigates crops so that they are always well-watered. For those crops, such as many of the agricultural crops that are grown in arid or semi-arid regions, if this endogenous ABA-response of the stomata were "turned off", crop yield could be increased, or the time for the plant to reach maturity decreased by removing the limits on increased $CO_2$ uptake and fixation.

Many crops, for example feed corn and wheat, are dried in the field before harvest. Other crops, such as tobacco and dried fruits such as raisins and prunes, are dried immediately post-harvest. It would be advantageous to growers to be able to accelerate or control the rate of crop drying.

For example, at the end of the growing season, it might be advantageous to dry the plants as quickly as possible, to minimize exposure to adverse weather conditions. However, water stress inevitably triggers ABA production/redistribution in the plant, leading to stomatal closure, which slows the rate of water loss, thus slowing the rate of crop drying.

Therefore, it would be advantageous to growers if this ABA-triggered stomatal closure response could be prevented or controlled.

In other cases, post-harvest, for many fruits, vegetables, and for cut-flowers, it is advantageous for the produce to dry out as slowly as possible, to retain freshness during transport, distribution, and purchase of the product. In these situations, it would be advantageous if the ABA-induced stomatal closure response could be enhanced. This could significantly extend the shelf life of the product.

The theoretical solution to the problems posed above is for growers to be able to precisely control the plant's transpiration via ABA-responsiveness of the guard cells/stomata. Ideally this control should be:

1. specific to the guard cells. It should not disrupt the many other effects of ABA on plant growth and development.

2. specific to ABA. There are many other stimuli that guard cells respond to in the control of stomatal aperture, for example, light and decreased intracellular concentrations of $CO_2$ drive stomatal opening, and conversely, darkness and high $CO_2$ concentrations drive stomatal closure. For crops under irrigation for example, the grower would still want the stomata to close in response to darkness, because in darkness there is no photosynthesis anyway, and open stomata during the night would simply waste irrigation water and thus money.

3. inducible, titratable, and reversible. To be of greatest utility, the grower would want to be able to control "when" and "how much" the guard cells respond to ABA. Ideally, the grower would be able to open and close the stomata depending on the prevailing environmental conditions and desired results for his crop.

In present practice, growers have only limited control of rates of water loss from plants, mainly by controlling irrigation regimens in the field, and controlling environmental conditions during shipping, handling and storage of the product. By capitalizing on the present invention, growers could choose when plants would retain their maximum hydrated status (e.g. during times of water restriction, or for shipping of fresh produce), and when plants could be induced to dry out more quickly (e.g. as required for crops that are dried in the field before harvest).

Mutants have been identified in *Arabidopsis*, which display reduced rates of ABA production (aba mutants; Koornneef et al. 1982, Theor. Appl. Genet. 61:385–393) or ABA sensing (abi mutants; Koomneef et al. 1984 Physiol. Plant. 61:377–383). While these plants exhibit increased rates of water loss, the mutations are pleiotropic and this is a disadvantage. For example, the aba and abi mutants have reduced seed dormancy, and so the viability of the seed is likely to be reduced, a severe problem limiting any commercial application.

The isolation of novel mutants and genes that encode altered ABA-mediation of transpirational water loss will broaden the range of options for growers. It would be particularly advantageous to isolate mutants or genes involved in altered ABA-mediation of transpiration without spontaneously occurring abnormal responses to other roles of ABA or abnormal responses to factors such as light levels and concentrations of $CO_2$. Novel regulatory mutants are likely to have distinct induction of unique subsets of genes. The isolation of mutants will yield the critical gene(s) involved with altered ABA-mediation of transpiration, which can be used to transgenically transfer the novel trait to other species.

SUMMARY OF THE INVENTION

Provided in the present invention is a novel nucleic acid molecule (referred herein as AAPK), which is associated with regulation of transpiration by the hormone abscisic acid (ABA) in plants. The invention further provides transgenic plants and mutants having modified ABA-mediated stomatal closure. In these plants, ABA-mediated stomatal closure is modified in a manner that is independent of $CO_2$- and light-mediated responses of transpiration, as measured by changes in stomatal aperture.

According to one aspect of the present invention, a nucleic acid molecule encoding an ABA-activated protein kinase, AAPK, is provided. An exemplary AAPK-encoding nucleic acid molecule of the invention is that of *Vicia faba*, a food crop of major importance in the Middle East. Also exemplified are homologs of the gene in *Arabidopsis thaliana*. The invention further provides homologs of the exemplified AAPK, having a level of nucleotide sequence or amino acid sequence identity with the exemplified AAPK nucleic acids or encoded AAPK proteins, specifically at certain regions of the coding sequence, that clearly distinguish the homologs as AAPK homologs, as opposed to other kinases. Preferably, these homologs comprise nucleotide or amino acid sequences at least 60%, preferably 67%, more preferably 70% and even more preferably 80% identical to the *Vicia faba* and *Arabidopsis* AAPK nucleic acid and AAPK amino acid sequences set forth herein.

Also provided in accordance with the present invention is a disrupted gene product of the AAPK gene. In a preferred embodiment, the disrupted gene product comprises lost or reduced activity of the AAPK protein. Reduction in amount or activity of AAPK in plants results in decreased sensitivity of the plants to ABA-induced stomatal closure, but does not affect the plants's sensitivity to dark- or $CO_2$-induced stomatal closure.

According to another aspect of the invention, an oligonucleotide molecule of at least 15 nucleotides in length, preferably at least 20 nucleotides in length, and most preferably at least 30 nucleotides in length, that is identical in sequence to a portion of an AAPK nucleic acid, is provided. In a preferred embodiment, the invention provides a nucleic acid molecule of at least 15, preferably 20, and most preferably 30 or more nucleotides in length, that is identical to or complementary to a consecutive 15, 20 or 30 nucleotide portion, respectively, of the sequence set out in one of SEQ ID NOS:1, 3 or 6.

According to other aspects of the invention, an isolated polypeptide produced by expression of a nucleic acid molecule of the invention is provided. Also featured are antibodies immunologically specific for such a polypeptide.

According to another aspect of the invention, a vector for transforming a plant cell, comprising a nucleic acid molecule of the invention, is provided. Also featured are plant cells transformed with the vector, and intact fertile plants regenerated from the plant cells. It will be appreciated by persons of skill in the art, that various portions of such genetically altered plants are also encompassed by the present invention. These include, but are not limited to, roots, modified roots (e.g., tubers), stems, leaves, flowers, fruits and seeds, and components thereof, e.g., extracts or oils.

According to another aspect of the invention, a genetically altered plant is provided, which possesses decreased sensitivity to ABA-induced stomatal closure as compared with an equivalent but unaltered plant. These genetically altered plants contain an AAPK that is largely nonfunctional or absent. In one embodiment, the plant is produced by subjecting a population of plants to mutagenesis and selecting a mutagenized plant wherein the AAPK is largely nonfunctional or absent. In a preferred embodiment, the plant is produced by transforming cells of the plant with a transgene that causes the plant's endogenous AAPK to become largely nonfunctional or absent, and regenerating the plant from the transformed cell. In a particularly preferred embodiment, expression of the transgene is inducible.

According to another aspect of the invention, a genetically altered plant possessing increased sensitivity to ABA-induced stomatal closure as compared with an equivalent but unaltered plant, is provided. Plants of this type contain an AAPK that is increased in amount or activity as compared with the unaltered plant. In one embodiment, these plants are produced by subjecting a population of plants to mutagenesis and selecting a mutagenized plant wherein the AAPK is largely nonfunctional or absent. In a preferred embodiment, the plants are produced by transforming cells of the plant with a transgene that causes the plant's endogenous AAPK to become largely nonfunctional or absent, and regenerating the plant from the transformed cells. In a particularly preferred embodiment, expression of the transgene is inducible.

Another aspect of the invention features a method to increase transpiration in a plant. The method comprises reducing or preventing function of an AAPK in guard cells of the plant, thereby reducing sensitivity of the plant to ABA-induced stomatal closure, resulting in the increased transpiration. Conversely, a method is provided to decrease transpiration in a plant, comprising increasing function of AAPK in guard cells of the plant, thereby increasing sensitivity of the plant to ABA-induced stomatal closure, resulting in decreased transpiration.

Other features and advantages of the present invention will be better understood by reference to the drawings, detailed description and examples that follow.

BRIEF DESCRIPTION OF THE DRAWINGS

FIG. 1. Alignment of the deduced AAPK amino acid sequence with those of homologous protein kinases. GenBank accession numbers for the nucleic acid molecules encoding the displayed amino acid sequences are: AAPK (AF186020), *Arabidopsis* Atpk (L05562, S71172), tobacco WAPK (AF032465), soybean SPK-4 (L38855), rice REK (AB002109), ice plant MK9 (Z26846), and wheat PKABA1 (M94726). Sequence ID Numbers for the displayed sequences are as follows: AAPK is SEQ ID NO:2 (encoded by SEQ ID NO:1); Atpk is SEQ ID NO:4 (encoded by SEQ ID NO:3); WAPK is SEQ ID NO: 11; SPK-4 is SEQ ID NO: 12; REK is SEQ ID NO:13; MK9 is SEQ ID NO:14; PKABA1 is SEQ ID NO: 10 (encoded by SEQ ID NO:9). Amino acids are highlighted when there are at least four identical residues among the seven sequences. Conserved subdomains of the protein kinase family are indicated by roman numerals. Peptide sequences obtained by tandem mass spectrometry are marked by lines. Peptide regions used for designing degenerate PCR primers are indicated by arrows. Sequences were aligned by the Clustal method in MegAlign (DNASTAR, Madison, Wis.). Numbers indicate amino acid positions.

FIG. 2. Alignment of the deduced amino acid sequence of AAPK from *Vicia faba* (SEQ ID NO:2) with the amino acid sequence of a homologous protein kinase from *Arabidopsis thaliana* (SEQ ID NO:5). Query sequence=AAPK (GI 6739629), Length=349 amino acids. Subject sequence=*A. thaliana* protein kinase, Length=357 amino acids [GenBank Accession Number CAA19877 (GI 3297819)]. Comparison was done using the Blast 2 alignment program at NCBI, with following default parameters: Matrix: BLOSUM62, Gap Penalties: Existence: 11, Extension: 1. Identities=270/348 (77%), Positives=311/348 (88%), Gaps=1/348 (0%). The sequence shown between the Query and the Subject sequences shows the consensus sequence. A letter indicates identity, a '+' indicates a similarity, while a blank space indicates the two sequences are different at that residue.

FIG. 3. Alignment of the deduced amino acid sequence of AAPK from *Vicia faba* (SEQ ID NO:2) with the deduced amino acid sequence from a gene encoding a homologous protein kinase from *Arabidopsis thaliana* (SEQ ID NO:7). Query sequence=AAPK (GI 6739629), Length=349 amino acids. Subject sequence=deduced amino acid sequence from *A. thaliana* L05561 clone, Length=362 amino acids [GenBank Accession Number L05561 (GI 166817)]. Comparison was done using the Blast 2 alignment program at NCBI, with following default parameters: Matrix: BLOSUM62, Gap Penalties: Existence: 11, Extension: 1. Identities=273/353 (77%), Positives=318/353 (89%), Gaps=4/353 (1%). The sequence shown between the Query and the Subject sequences shows the consensus sequence. A letter indicates identity, a '+' indicates a similarity, while a blank space indicates the two sequences are different at that residue.

FIG. 4. Alignment of the deduced amino acid sequence of AAPK from *Vicia faba* (SEQ ID NO:2) with the amino acid sequence of a homolog, Protein Kinase SPK-2, from *Arabidopsis thaliana* (SEQ ID NO:8). Query sequence=AAPK (GI 6739629), Length=349 amino acids. Subject sequence=amino acid sequence from *A. thaliana*, Length=362 amino acids [GenBank Accession Number S56718 (GI 1362002)]. Comparison was done using the Blast 2 alignment program at NCBI, with following default parameters: Matrix: BLOSUM62, Gap Penalties: Existence: 11, Extension: 1. Identities=273/353 (77%), Positives=318/353 (89%), Gaps=4/353 (1%). The sequence shown between the Query and the Subject sequences shows the consensus sequence. A letter indicates identity, a '+' indicates a similarity, while a blank space indicates the two sequences are different at that residue.

DETAILED DESCRIPTION OF THE INVENTION

I. Definitions

Various terms relating to the biological molecules of the present invention are used hereinabove and also throughout the specifications and claims.

With respect to the genotypes of the invention, the term "AAPK" is used to designate the naturally-occurring or wild-type genotype. This genotype has the phenotype of naturally-occurring sensitivity to the effects of ABA. Where used hereinabove and throughout the specifications and claims, the term "AAPK" refers to the protein product of the AAPK gene.

In reference to the mutants of the invention, the term "null mutant" or "loss-of-function mutant" is used to designate an organism or genomic DNA sequence with a mutation that causes the product of the gene of interest to be nonfunctional or largely absent. Such mutations may occur in the coding and/or regulatory regions of the gene of interest, and may be changes of individual residues, or insertions or deletions of regions of nucleic acids. These mutations may also occur in the coding and/or regulatory regions of other genes which may regulate or control the gene of interest and/or its encoded gene product so as to cause said gene product to be non-functional or largely absent.

With reference to certain of the DNA constructs of the invention, the terms "pGFP", "pAAPK-GFP" and "pAAPK (K43A)-GFP" refer to constructs made from the green fluorescent protein (GFP) expression vector, pGFP, which allows cells transformed with the pGFP to express the readily-detected green fluorescent protein. Where used herein, "pAAPK-GFP" refers to a pGFP expression vector with the sequence encoding AAPK inserted upstream of and in-frame with the sequence encoding the GFP, such that both proteins can be expressed in cells transformed with this construct. Where used herein, "pAAPK(K43A)-GFP" refers to a pGFP expression vector with the sequence encoding an AAPK, modified such that the lysine residue at position 43 in the ATP binding site is changed to an alanine, inserted upstream of and in-frame with the sequence encoding the GFP, such that both proteins can be expressed in cells transformed with this construct.

With reference to nucleic acids of the invention, the term "isolated nucleic acid" is sometimes used. This term, when applied to genomic DNA, refers to a DNA molecule that is separated from sequences with which it is immediately contiguous (in the 5' and 3' directions) in the naturally-occurring genome of the organism from which it was derived. For example, the "isolated nucleic acid" may comprise a DNA molecule inserted into a vector, such as a plasmid or virus vector, or integrated into the genomic DNA of a procaryote or eukaryote. An "isolated nucleic acid molecule" may also comprise a cDNA molecule or a synthetic DNA molecule.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

Nucleic acid sequences and amino acid sequences can be compared using computer programs that align the similar sequences of the nucleic or amino acids thus define the differences. In preferred methodologies, the BLAST programs (NCBI) and parameters used therein are employed to align nucleotide and amino acid sequences. However, equivalent alignments and similarity/identity assessments can be obtained through the use of any standard alignment software. For instance, the DNAstar system (Madison, Wis.) may be used to align sequence fragments of genomic or other DNA sequences. Alternatively, GCG Wisconsin Package version 9.1, available from the Genetics Computer Group in Madison, Wis., and the default parameters used (gap creation penalty=12, gap extension penalty=4) by that program may also be used to compare sequence identity and similarity.

The term "substantially the same" refers to nucleic acid or amino acid sequences having sequence variation that do not materially affect the nature of the protein (i.e. the structure, stability characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined by Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form. In this regard, "isolated" or "isolated and purified" also refers to its separation or removal from a chromatography column matrix or a gel, such as a polyacrylamide gel. That is, a polypeptide that has been separated by chromatography or polyacrylamide gel electrophoresis, but is not eluted from the matrix or gel, is not considered "isolated" or "isolated and purified".

With respect to antibodies of the invention, the terms "immunologically specific" or "specific" refer to antibodies that bind to one or more epitopes of a protein of interest, but which do not substantially recognize and bind other molecules in a sample containing a mixed population of antigenic biological molecules.

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

II. Description

In accordance with the present invention, an isolated nucleic acid molecule is provided that encodes a novel regulator of ABA-mediated stomata aperture control. This nucleic acid molecule is referred to herein as AAPK ("ABA-activated protein kinase"). Its manner of regulating ABA-mediated stomata aperture control is novel and interesting. When the functional product of the gene is eliminated or specifically altered in a plant, the plant exhibits decreased sensitivity to ABA-induced stomatal closure, but without changing the plant's responses to stomatal closure induced by darkness or $CO_2$. In addition, the loss of function of AAPK had no effect on ABA-mediated inhibition of stomatal opening. While not intending to limit the present invention by describing one possible mechanism of action of AAPK, it may be that AAPK functions as a negative regulator of ABA-mediated stomatal aperture control, and resultant transpiration and gas exchange.

AAPK was selected as an important target for cloning firstly because its ABA-activated phosphorylation activity is specific to guard cells. Secondly, AAPK was selected because it was not activated by other stoma-closing factors such as $CO_2$ or darkness, making it a potential guard cell-specific, ABA response regulator of stomatal closure. Furthermore, since maintaining control of transpirational water loss and gas exchange is of a vital and fundamental nature to plants, AAPK is likely to be a highly conserved function among all plant species.

The AAPK cDNA was isolated from a *Vicia faba* cDNA library by using degenerate primers created based on peptide sequence data. The degenerate primers were used in reverse transcriptase—PCR to generate a 310 bp probe from guard cell RNA. The probe was then used to screen a *V. faba* guard cell cDNA library. Based on analysis of the probes, the AAPK gene product appears to be a significant protein kinase in the guard cells, inasmuch as other protein kinases were not identified despite the fact that the probe was homologous to domains common to other protein kinase family members. Sequence analysis of this cDNA revealed the nucleic acid sequence of SEQ ID NO:1, and a predicted polypeptide sequence having SEQ ID NO:2. The deduced amino acid sequence was compared to PKABA1 (SEQ ID NO:10), the expressed product of an ABA-induced transcript from wheat (Anderberg & Walker-Simmons, Proc. Natl. Acad. Sci. USA 89: 10183–10187, 1992). PKABA1 is a known protein kinase with conserved regions common to this family of kinases. Comparison with PKABA1 revealed that AAPK also possesses these conserved kinase domains.

Figure 1:
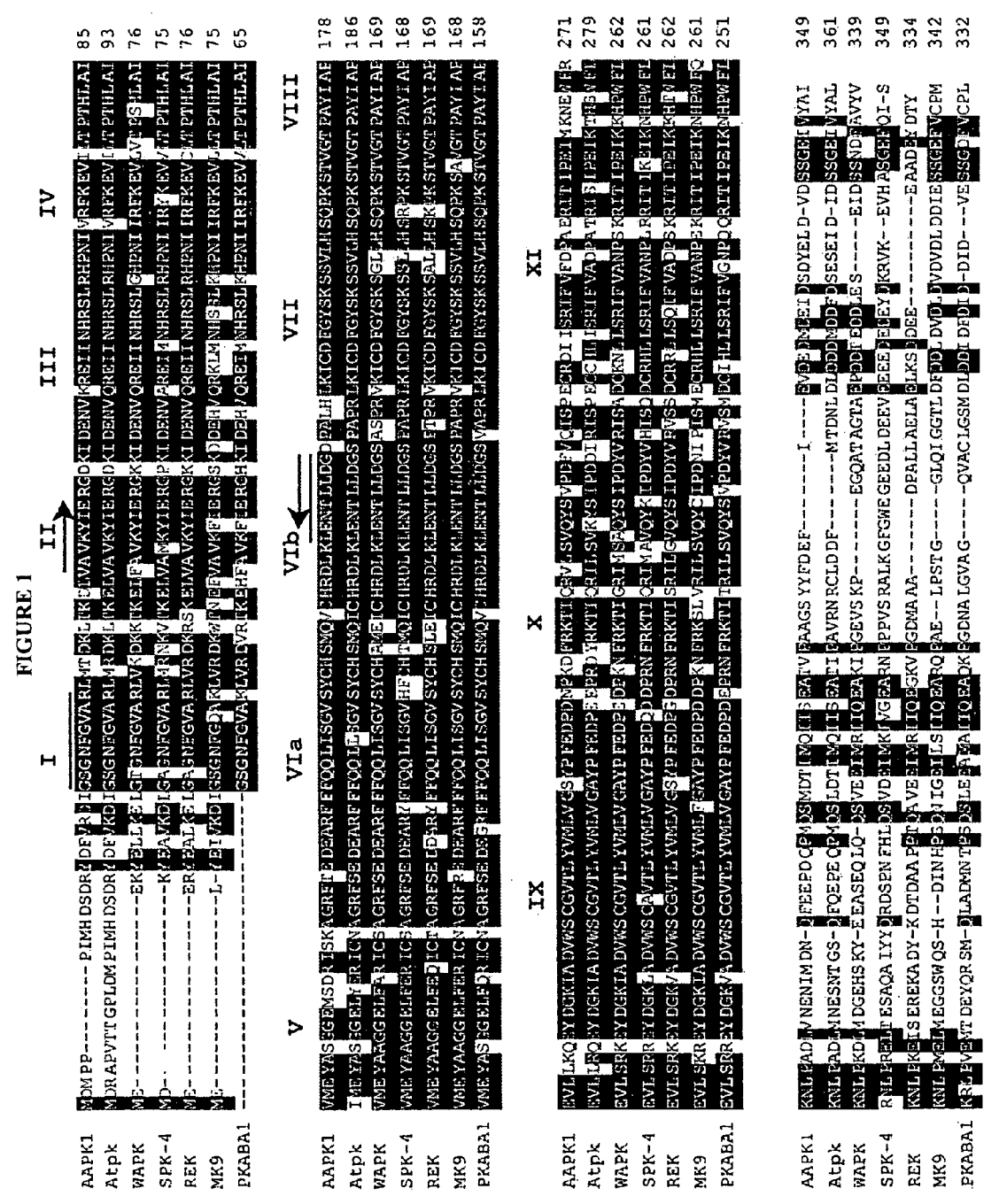

Many diverse protein kinases are involved in cascading cellular signal transduction; however the kinase domain is highly conserved in all protein kinases. The AAPK protein sequence contains high similarity to a large number of protein kinases, as revealed, for example, by the alignment of plant protein kinases shown in FIG. 1. The functional specialization that allows these kinases to operate in specific signal transduction pathways lies both in the kinase domain and non-kinase domains. The *Vicia faba* AAPK kinase protein (SEQ ID NO:2) displays significant similarity to PKABA1 (SEQ ID NO:10). While the similarity is highest in the putative kinase domains, there are several regions where the two proteins are less different from one another. PKABA is expressed from an ABA-induced transcript, but it has not been shown to possess the ABA-activated protein kinase activity of AAPK, suggesting that it plays a different role.

As described in Example 2, genomic screening of an *Arabidopsis* library and GenBank database screening using the SEQ ID NO:1 cDNA reveals that the *Vicia faba* AAPK is most similar to the proteins (SEQ ID NOS: 4, 5 and 7) encoded by the *Arabidopsis* genes having Genbank Accession Numbers L05561 and L05562, and *Arabidopsis* protein having Accession No. CAA19877, respectively, indicating that these genes and proteins are clear functional homologs of *Vicia faba* AAPK and its encoded protein.

An additional round of database screening was performed, using peptide segments of SEQ ID NO:2 that were homologous to SEQ ID NO: 4 (encoded by GenBank L05562, *Arabidopsis* Atpk) but different from wheat PKABA1 (SEQ ID NO:10). These peptides were: (1) PIM-HDSDRYDF (SEQ ID NO:15), corresponding to residues 5–15 of SEQ ID NO:2 at the amino terminus; and (2)=PADLVNENIMDNQFEEPDQ (SEQ ID NO;16), corresponding to residues 275–293 of SEQ ID NO:2 near the carboxyl terminus. Screening with either of these peptides corroborated the physical and database screening using the complete sequence, identifying each the aforementioned *Arabidopsis* proteins. This screening also revealed a fourth homolog, identified in the database as Protein Kinase SPK-2, Accession No. S56718 (SEQ ID NO:8). It is possible that this *Arabidopsis* protein is the same as the predicted protein from clone L05561.

Although the AAPK cDNA clone from *Vicia faba*, and homologs from *Arabidopsis* are described and exemplified herein, this invention is intended to encompass nucleic acid sequences and proteins from other plants that are sufficiently similar to be used instead of the *Vicia faba* or *Arabidopsis* AAPK nucleic acids and proteins for the purposes described below. These include, but are not limited to, allelic variants and natural mutants of AAPK, which are likely to be found in different varieties of *Vicia faba*, as well as homologs of AAPK from different species of plants. Because such variants and homologs are expected to possess certain differences in nucleotide and amino acid sequence, this invention provides an isolated AAPK nucleic acid molecule having at least about 50% (preferably 60%, more preferably 70% and even more preferably over 80%) sequence identity in the coding regions with the nucleotide sequence set forth as SEQ ID NOs:1, 3, 5, 7 or 9 (and, most preferably, specifically comprising the coding regions of SEQ ID NOs:1, 3, or 6 This invention also provides isolated polypeptide products of the open reading frames of AAPK, having at least about 60% (preferably 70%, 75%, 80% or greater) sequence identity with the amino acid sequences of SEQ ID NOS: 2, 4, 5, 7 or 9. Because of the natural sequence variation likely to exist among AAPK genes, one skilled in the art would expect to find up to about 30–40% nucleotide sequence variation, while still maintaining the unique properties of the AAPK nucleic acid molecules and encoded polypeptides of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention. Within the parameters of sequence identity and similarity set forth above, AAPKs from any plant species are considered part of the present invention. Such plant species include dicotyledenous and monocotyledenous flowering plants, as well as any other plant that possesses stomata. Of particular importance to the invention are AAPKs from agronomically or horticulturally important plant species, including maize, wheat, rye, oats, barley, rice, sorghum, soy and other beans, alfalfa, sunflower, canola, lawn and turfgrasses, tobacco, aster, zinnia, chrysanthemum, beet, carrot, cruciferous vegetables, cucumber, grape, pea, potato, rutabaga, tomato, tomatillo and turnip, to name a few.

AAPK nucleic acid molecules of the invention include DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule encoding the protein of the present invention. Such oligonucleotides are useful as probes for detecting AAPK genes or transcripts.

In addition to encompassing natural mutants of AAPK, the present invention is drawn to artificially created mutants, produced by in vitro mutagenesis or isolated from mutagenized plants, as described in greater detail below. These mutant AAPK nucleic acids and their encoded proteins are integral to practicing the methods of the invention, which involve regulating ABA-mediated stomatal closure in plants. The present invention further encompasses genetically modified plants having altered transpiration and gas exchange characteristics due to the down-regulation or up-regulation of AAPK in those plants.

The following sections set forth the general procedures involved in practicing the present invention in all of its aspects as summarized above. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (2000) (hereinafter "Ausubel et al.") are used.

A. Preparation of AAPK Nucleic Acids, Proteins, Antibodies, AAPK Mutants and Transgenic Plants Preparation of AAPK Nucleic Acid Molecules. AAPK nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such SEQ ID NOS: 1, 3 and 6, enables preparation of an isolated nucleic acid molecule of the invention by polynucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

Modified (i.e., "mutant") nucleic acid molecules of the invention also may be synthesized as described above. In this embodiment, the desired alteration is simply programmed into the synthetic scheme. In another embodiment, an unaltered synthetic nucleic acid molecule is manufactured, and subsequently altered by site-directed mutagenesis.

Nucleic acid molecules encoding the AAPK protein may be isolated from *V. faba, Arabidopsis* or any other plant of interest using methods well known in the art. It will be appreciated that such methods may be used to screen libraries of mutant plants as well as wild-type plants. In order to isolate AAPK-encoding nucleic acids from plants other than *V. faba*, or *Arabidopsis*, oligonucleotides designed to match the nucleic acids encoding the *V. faba* or *Arabidopsis* AAPK protein may be used with cDNA or genomic libraries from the desired species. If the AAPK gene from a species is desired, the genomic library is screened. Alternately, if the protein coding sequence is of particular interest, the cDNA library is screened. In positions of degeneracy, where more than one nucleic acid residue could be used to encode the appropriate amino acid residue, all the appropriate nucleic acids residues may be incorporated to create a mixed oligonucleotide population, or a neutral base such as inosine may be used. Such degenerate libraries also may be customized for the codon preference of the plant species to be screened. The strategy of oligonucleotide design is well known in the art (see Ausbel et al., Sambrook et al.).

In another embodiment, known AAPK sequences may be used in "data mining" to screen databases for homologous sequences, as is well known in the art and exemplified herein.

Alternatively, PCR (polymerase chain reaction) primers may be designed by the above method to encode a portion a known AAPK protein, and these primers used to amplify nucleic acids from isolated cDNA or genomic DNA. In a preferred embodiment, the oligonucleotides used to isolate AAPK nucleic acids are designed to encode sequences conserved among AAPKs, but not between AAPK and other kinases (e.g., the PKABA1 protein kinase family), as described above.

In accordance with the present invention, nucleic acids having the appropriate sequence homology with a known AAPK nucleic acid molecule may be identified by using hybridization and washing conditions of appropriate stringency. For example, hybridizations may be performed, according to the method of Sambrook et al. (1989, supra), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology (Sambrook et al.) is:

$$T_m = 81.5°C + 16.6 \log [Na+] + 0.41(\% G+C) - 0.63(\% \text{formamide}) - 600 \text{\#bp in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. In a preferred embodiment, the hybridization is at 37° C. and the final wash is at 42° C., in a more preferred embodiment the hybridization is at 42° C. and the final wash is at 50° C., and in a most preferred embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable *E. coli* host cell.

Preparation of polypeptides and antibodies. AAPK polypeptides may be prepared in a variety of ways, according to known methods. The availability of nucleic acid molecules encoding the polypeptides enables synthesis of the proteins by known methods, or production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md. The pCITE in vitro translation system (Novagen) also may be utilized.

According to a preferred embodiment, larger quantities of the proteins may be produced by expression in a suitable procaryotic or eucaryotic system. For example, part or all of a DNA molecule, such as the coding portion of SEQ ID NOS: 1, 3 or 6, or appropriate complementary sequences, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The AAPK polypeptides produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

AAPK proteins, prepared by the aforementioned methods, may be analyzed according to standard procedures. Methods for analyzing the functional activity of kinases are well known to persons skilled in the art. Alternatively, the function of the kinase in stomatal closure may be analyzed, as described in greater detail below and in Example 1.

The present invention also provides antibodies that are immunologically specific to the AAPK of the invention. Polyclonal antibodies may be prepared according to standard methods. In a preferred embodiment, monoclonal antibodies are prepared, which are specific to various epitopes of the protein. Monoclonal antibodies may be prepared according to general methods of Köhler and Milstein, following standard protocols. Polyclonal or monoclonal antibodies that are immunologically specific for the AAPK can be utilized for identifying and purifying AAPK from *V. faba* and other species. For example, antibodies may be utilized for affinity separation of proteins for which they are specific or to quantify the protein. Antibodies may also be used to immunoprecipitate proteins from a sample containing a mixture of proteins and other biological molecules.

Mutants and transgenic plants. Example 1 describes a synthetic mutant, AAPK(K43A) in *Vicia faba*, which displays insensitivity to ABA-induce stomatal closure due to the loss of function of AAPK. Any plant may be transgenically engineered to display a similar phenotype. This approach is particularly appropriate to plants with high ploidy numbers, including but not limited to wheat.

These synthetic null mutant are created by a expressing a mutant form of the AAPK protein to create a "dominant negative effect". While not limiting the invention to any one mechanism, this mutant AAPK protein competes with wild-type AAPK protein for interacting proteins in the transgenic plant, or poisons an AAPK multimeric complex. By over-producing the mutant form of the protein, the signaling pathway used by the wild-type AAPK protein can be effectively blocked. Examples of this type of "dominant negative" effect are well known for both insect and vertebrate systems (Radke et al, 1997, Genetics 145:163–171; Kolch et al., 1991, Nature 349:426–428). In a preferred embodiment, the mutant protein is produced by mutating the coding sequence of AAPK corresponding to residues in the active site. In a particularly preferred embodiment, the coding sequence corresponding to the lysine residue at position 43 is mutated to code for a different, preferably non-similar, amino acid residue, for example, alanine.

A second kind of synthetic null mutant can be created by inhibiting the translation of the AAPK mRNA by "post-transcriptional gene silencing". The AAPK gene from the species targeted for down-regulation, or a fragment thereof, may be utilized to control the production of the encoded protein. Full-length antisense molecules or antisense oligonucleotides are used that are targeted to specific regions of the AAPK-encoded RNA that are critical for translation. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95:13959–13964). In a preferred embodiment, part or all of the AAPK coding sequence antisense strand is expressed by a transgene. In a particularly preferred embodiment, hybridizing sense and antisense strands of part or all of the AAPK coding sequence are transgenically expressed.

A third type of synthetic null mutant can also be created by the technique of "co-suppression". Plant cells are transformed with a copy of the endogenous gene targeted for repression. In many cases, this results in the complete repression of the native gene as well as the transgene. In a preferred embodiment, the AAPK gene from the plant species of interest is isolated and used to transform cells of that same species.

Transgenic plants can also be created that have enhanced AAPK activity. This can be accomplished by transforming plant cells with a transgene that expresses part or all of the AAPK coding sequence, or a sequence that encodes the either the AAPK protein or a protein functionally similar to it. In a preferred embodiment, the complete AAPK coding sequence is transgenically over-expressed. In another embodiment, the coding sequence corresponding to the kinase domain of AAPK is over-expressed.

Transgenic plants with one of the transgenes mentioned above can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 (Bevan, 1984) and derivatives thereof, the pBI vector series (Jefferson et al., 1987), and binary vectors pGA482 and pGA492 (An, 1986) For transformation of monocot species, biolistic bombardment with particles coated with transforming DNA and silicon fibers coated with transforming DNA are often useful for nuclear transformation.

DNA constructs for transforming a selected plant comprise a coding sequence of interest operably linked to appropriate 5' (e.g., promoters and translational regulatory sequences) and 3' regulatory sequences (e.g., terminators). In a preferred embodiment, the coding region is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase (NOS) and octopine synthase (OCS) promoters.

Transgenic plants expressing a sense or antisense AAPK coding sequence under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name a few.

Tissue specific and development-specific promoters are also contemplated for use in the present invention. Examples of these included, but are not limited to: the ribulose bisphosphate carboxylase (RuBisCo) small subunit gene promoters or chlorophyll a/b binding protein (CAB) gene promoters for expression in photosynthetic tissue; the various seed storage protein gene promoters for expression in seeds; and the root-specific glutamine synthetase gene promoters where expression in roots is desired. Although the AAPK gene of the preferred embodiments taught with this invention are specifically expressed in guard cells, this in no way limits the application of this invention to any specific tissue or development phase, but rather represents only the particular embodiments taught herein.

The coding region is also operably linked to an appropriate 3' regulatory sequence. In a preferred embodiment, the nopaline synthetase polyadenylation region (NOS) is used. Other useful 3' regulatory regions include, but are not limited to the octopine (OCS) polyadenylation region.

Using an *Agrobacterium* binary vector system for transformation, the selected coding region, under control of a constitutive or inducible promoter as described above, is linked to a nuclear drug resistance marker, such as kanamycin resistance. Other useful selectable marker systems include, but are not limited to: other genes that confer antibiotic resistances (e.g., resistance to hygromycin or bialaphos) or herbicide resistance (e.g., resistance to sulfonylurea, phosphinothricin, or glyphosate).

Plants are transformed and thereafter screened for one or more properties, including the lack of AAPK protein, AAPK mRNA, or altered stomatal aperture responses to ABA treatment. It should be recognized that the amount of expression, as well as the tissue-specific pattern of expression of the transgenes in transformed plants can vary depending on the position of their insertion into the nuclear genome. Such positional effects are well known in the art. For this reason, several nuclear transformants should be regenerated and tested for expression of the transgene.

Transgenic plants that exhibit one or more of the aforementioned desirable phenotypes can be used for plant breeding, or directly in agricultural or horticultural applications. Plants containing one transgene may also be crossed with plants containing a complementary transgene in order to produce plants with enhanced or combined phenotypes.

An alternative to the transgenic approach described above is the screening of populations of plant mutants of a variety of species, from which AAPK mutants can be isolated. Such populations can be made by chemical mutagenesis, radiation mutagenesis, and transposon or T-DNA insertion, as is well known in the art. In a preferred embodiment, the mutants would be null mutants having a phenotype comprising reduced or substantially absent stomatal closure in response to abscisic acid, but no reduction in stomatal closure response to darkness or $CO_2$. In yet another preferred embodiment, mutant are screened for the phenotypes related to overproduction of the AAPK gene product and/or increased sensitivity to ABA-induced stomatal closure.

The nucleic acids of the invention can be used to isolate or create AAPK mutants in a selected species. In species such as maize where transposon insertion lines are available, oligonucleotide primers can be designed to screen lines for insertions in the AAPK gene. Plants with transposon or T-DNA insertions in the AAPK gene are very likely to have lost the function of the gene product. Through breeding, a plant line may then be developed that is homozygous for the non-functional copy or the altered copy of the AAPK gene. The PCR primers for this purpose are designed so that large portions of the coding sequence the AAPK gene are specifically amplified using the sequence of the AAPK gene from the species to be probed (see Baumann et al., 1998, Theor. Appl. Genet. 97:729–734).

Other AAPK-like mutants can be isolated from mutant populations using the distinctive phenotype characterized in accordance with the present invention. This approach is particularly appropriate in plants with low ploidy numbers where the phenotype of a recessive mutation is more easily detected. In order to identify these mutants, the population of plants would be exposed to abscisic acid (ABA) or analogs of the hormone. Plants would then be screened for phenotype of the AAPK mutants: the reduced stomatal closure in response to applied ABA, without a reduction in stomatal response to darkness or $CO_2$. That the phenotype is caused by an AAPK mutation is then established by molecular means well known in the art.

It will be appreciated that any of the aforementioned transformation or mutagenesis techniques may be applied to any selected plant species. Such species include, but are not limited to, agronomically important crop plants such as maize, wheat, rice, rye, oats, barley, soy and other beans, sorghum, sunflower, canola, tobacco and alfalfa; vegetable and fruit crop plants such as beet, carrot, cruciferous vegetables, cucumber, grape, pea, potato, rutabaga, tomato, tomatillo and turnip; and horticulturally important plants such as aster, begonia, chrysanthemum, clover, lawn and turf grasses, mint and other herbs, and zinnia.

B. Uses of AAPK Nucleic Acids, Proteins, Antibodies, AAPK Mutants and Transgenic Plants Nucleic acid molecules. AAPK nucleic acids may be used for a variety of purposes in accordance with the present invention. DNA, RNA, or fragments thereof, may be used as probes to detect the presence and/or expression of AAPK genes. Methods in which AAPK nucleic acids may be utilized as probes for such assays include, but are not limited to: (1) in situ hybridization; (2) Southern hybridization (3) Northern hybridization; and (4) assorted amplification reactions such as polymerase chain reactions (PCR).

The AAPK nucleic acids of the invention may also be utilized as probes to identify related genes from other plant species. As is well known in the art, hybridization stringencies may be adjusted to allow hybridization of nucleic acid probes with complementary sequences of varying degrees of homology. As described above, AAPK nucleic acids may be used to advantage to produce large quantities of substantially pure AAPK, or selected portions thereof. The AAPK nucleic acids can be used to identify and isolate other putative members of this novel ABA-mediated stomatal aperture control signal cascade in vivo. A yeast two hybrid system can be used to identify proteins that physically interact with the AAPK protein, as well as isolate their nucleic acids. In this system, the sequence encoding the protein of interest is operably linked to the sequence encoding half of a activator protein. This construct is used to transform a yeast cell library which has been transformed with DNA constructs that contain the coding sequence for the other half of the activator protein operably linked to a random coding sequence from the organism of interest. When the protein made by the random coding sequence from the library interacts with the protein of interest, the two halves of the activator protein are physically associated and form a functional unit that activates the reporter gene. In accordance with the present invention, all or part of the AAPK coding sequence may be operably linked to the coding sequence of the first half of the activator, and the library of random coding sequences may be constructed with cDNA from *V. faba* and operably linked to the coding sequence of the second half of the activator protein. Several activator protein/reporter genes are customarily used in the yeast two hybrid system. In a preferred embodiment, the bacterial repressor LexA DNA-binding domain and the Gal4 transcription activation domain fusion proteins associate to activate the LacZ reporter gene (see Clark et al., 1998, PNAS 95:5401–5406). Kits for the two hybrid system are also commercially available from Clontech, Palo Alto Calif., among others.

In a preferred embodiment, interaction cloning is used identify proteins that physically interact with the AAPK protein and to isolate the nucleic acids encoding them. In this method, a cDNA expression library is screened for proteins that interact with the AAPK catalytic domain, or other selected domains that might be involved in protein—protein interactions. This is done using a filter binding assay and a labeled peptide comprising the putative interacting site. Positive clones are then purified, amplified if necessary, and characterized.

Proteins and antibodies. The AAPK proteins of the present invention can be used to identify molecules with binding affinity for AAPK, which are likely to be novel participants in this resistance pathway. In these assays, the known protein is allowed to form a physical interaction with the unknown binding molecule(s), often in a heterogenous solution of proteins. The known protein in complex with associated molecules is then isolated, and the nature of the associated protein(s) and/or other molecules is determined.

AAPK may also be generated as part of a fusion protein with one or more other proteins, for example with a green fluorescent protein (GFP). Such fusion products may have utility from either or each part of the fusion molecule. For example, the easy detection of their presence is provided by the GFP moiety, while the specific kinase activity is retained by the AAPK moiety. Additionally they may allow convenient use of commercially available antibodies specific to the fused portion (e.g antiGFP antibodies are readily available.)

Antibodies that are immunologically specific for AAPK may be utilized in affinity chromatography to isolate the AAPK protein, to identify or quantify the AAPK protein utilizing techniques such as western blotting and ELISA, or to immuno-precipitate AAPK from a sample containing a mixture of proteins and other biological materials. The immuno-precipitation of AAPK is particularly advantageous when utilized to isolate affinity binding complexes of AAPK, as described above.

Mutants and Transgenic Plants. The AAPK mutants of the invention display altered sensitivity to ABA-induced stomatal closure, and therefore can be used to improve crop and horticultural plant species. The AAPK mutants taught in this invention are particularly valuable in that the mutation is very specific. The altered sensitivity is found only in guard cells, and stomatal closure by other means such as darkness or $CO_2$ is unaffected. Such mutants will therefore be particularly useful in crop and horticultural varieties in which reduction of moisture content is important. Examples of such crops include but are not limited to cereal grains such as corn, wheat, rye, oats, barley, and rice, soybeans and other beans, as well as other products such as hay and commercial seed. In most of these cases failure to adequately dry the crop due to weather or other conditions results in substantial losses. In other cases including but not limited to tobacco, dried fruits such as raisins and prunes, nuts, coffee, tea, cocoa, and many ornamental goods, the produce needs to be dried immediately after harvest prior and to use. In these cases again, the mutants of this invention may be of tremendous value to growers who could accelerate or control the rate of crop drying.

The AAPK mutants exhibit a decreased induction by ABA of normal stomatal closure. They therefore have influence over transpirational water loss in plants. It is therefore contemplated that in addition to the specific applications mentioned heretofore, these mutants will have myriad applications to other important plant problems especially in irrigated crops or other crops where water and yield are delicately balanced.

It is also trivial to one skilled in the art to extend this invention to the production of mutants with increased sensitivity to ABA-induced stomatal closure. These mutants are useful for a variety agronomic purposes. It is clear that such mutants would keep the stomatal aperture small, and would therefore experience reduced transpirational water loss. Such mutants can be used to help enhance tolerance to water stress or drought conditions. Such mutants could be the result of active site changes or modifications which allow them to respond to lower concentrations of ABA, or they could be the result of mutations in genes in a common regulatory pathway. Such mutants could also be the result of overexpression of the AAPK gene product via a transgenic modification such that expression of AAPK is driven by an inducible promoter, a strong, highly active constitutive promoter, or by increasing the copy number of the gene in the plant. These approaches are all conceptually simple to one skilled in the art, and other approaches may be preferred for particular embodiments.

The AAPK mutants of the invention can be used to identify and isolate additional members of this ABA-regulation of transpiration pathway. Mutations that, when combined with AAPK mutations, suppress the mutant phenotype, are likely to interact directly with AAPK, or to compensate in some significant indirect way for the loss of AAPK function. Since AAPK is known to be a protein kinase with both autophosphorylation and substrate phosphorylation, there are opportunities to identify other important members of the ABA signal cascade using the mutants of this present invention.

The transgenic plants of the invention are particularly useful in conferring the AAPK phenotype to many different plant species. In this manner, a host of plant species with enhanced disease resistance can be easily made, to be used as breeding lines or directly in commercial operations. Such plants can have uses as crop species, or for ornamental use.

A plant that has had functional AAPK transgenically depleted will exhibit the same altered sensitivity to ABA-induced stomatal closure as AAPK mutants. It is therefore contemplated that transgenic AAPK-phenotype plants will be used with in the same aforementioned manner as the AAPK mutants. A transgenic approach is advantageous because it allows AAPK-phenotype plants to be created quickly, without time-consuming mutant generation, selection, and back-crossing.

A plant that has had functional AAPK increased may have enhanced sensitivity to ABA-induced stomatal closure compared to wild-type plants. Plants with enhanced sensitivity to ABA-induced stomatal closure will be extremely valuable to agriculture and horticulture by allowing plants to better tolerate periods of restricted water or drought. Additionally, such mutants may provide the advantage of allowing produce to retain water as long as possible. For many fruits, vegetables and flowers, including cut flowers, it would be advantageous to minimize water loss during the harvest, transport and distribution. Retail customers too would benefit from the extended shelf-life of such fruits, vegetables and flowers which would remain fresher for longer periods of time.

The following examples are provided to describe the invention in greater detail. They are intended to illustrate, not to limit, the invention.

EXAMPLE 1

Cloning and Characterization of ABA-Activated Protein Kinase-Encoding cDNA from Guard Cells This example describes the cloning and characterization of a *Vicia faba* complementary DNA, AAPK, encoding a guard cell-specific ABA-activated serine-threonine protein kinase (AAPK).

Methods

Isolation and Identification of ABA-Activated Protein Kinase (AAPK). Guard cell protoplasts ($2 \times 10^6$; 99.6% pure) were prepared from *Vicia faba*. Protoplasts were treated with either darkness, ABA or elevated $CO_2$ concentrations prior to protein isolation. Protoplast proteins were extracted and subjected to 2-dimensional gel electrophoresis. Separation was via 12% SDS-polyacrylamide gel electrophoresis (SDS-PAGE). Kinase autophosphorylation activity of subsequently renatured proteins was detected by established methods.

The AAPK protein was excised from the 2-D gels (first dimension, nondenaturing PAGE) after digestion with trypsin. The AAPK peptides generated by trypsin digestion were subjected to peptide sequencing by tandem mass spectrometry on a Finnigan LCQ quadrupole ion trap mass spectrometer.

Cloning of ABA-Activated Protein Kinase (AAPK).

The gene encoding AAPK was cloned by screening a *V. faba* cDNA library with probes constructed based on peptide sequence data obtained from the mass spectrometry analysis.

Degenerate DNA primers whose design was based on sequences conserved between subdomain II of the protein kinase ABA1 (PKABA1) protein kinase subfamily and the AAPK sequence corresponding to protein kinase subdomain VIb, were synthesized. The degenerate primers {5'-TTGC(C/T)(A/G)T(G/C) AA(A/G)TACATCGAA-3' (SEQ ID NO:17) (forward primer, located in subdomain II), 5'-CCATC(C/T)A(A/G)NAGNGT(A/G)TTTTC-3' (SEQ ID NO:18)(reverse primer, located in subdomain VIb) where N=A+G+C+T} were used for reverse transcription-polymerase chain reaction (RT-PCR) using as template total RNA from guard cells. of *V. faba*. The PCR product was labelled with {$^{32}$P}dCTP.

This $^{32}$P-labelled probe was then used to screen a *V. faba* guard cell cDNA library in λ-Zap II. A full length cDNA of the appropriate size to encode the AAPK was obtained. The cDNA was sequenced in both directions.

Total RNA was isolated from purified guard cells, mesophyll cells, flowers, leaves and seeds of *V. faba*. Northern analysis was performed by standard methods. The probe was the $^{32}$P-labelled BglII-Csp45I fragment of the AAPK cDNA clone. This probe includes the sequence encoding the relatively unique AAPK amino terminal region and part of the 3' untranslated region of the cDNA.

Functional Analysis of the AAPK gene. Functional analysis of the AAPK gene product was complicated by the observation that ABA-activation of the AAPK does not occur in vitro. Prior treatment of intact guard cells with ABA was required to elicit active AAPK upon extraction. In light of this apparent requirement for an intact cellular signal system, DNA constructs were created to facilitate the analysis of expression and activity of AAPK.

Creation of AAPK mutants and hybrid expression DNA constructs. A construct encoding a green fluorescent protein (GFP)-tagged AAPK was made. This construct, pAAPK-GFP, was created by amplifying the AAPK coding sequence from the AAPK cDNA and inserting the amplified coding sequence downstream of the 35S promoter and upstream of, and in-frame with, the GFP coding sequence in the GFP expression vector, pGFP. The amplification was performed via PCR with the primers 5'-GAATCTCCACTACGACGC-CGTTTACTTCCC-3' (SEQ ID NO:19) and 5'-CCGTG-CAACCATGGATATGGCATATACAAT-3' (SEQ ID NO:20). NcoI was used for digestion and insertion.

Another DNA construct, pAAPK(K43A)-GFP was created. This construct contained a site-directed mutation of AAPK, such that the coding sequence for a highly conserved lysine residue ($Lys^{43}$), believed to be in the ATP-binding site of the kinase AAPK, was specifically modified to encode an alanine residue instead of the lysine. Such mutations have been shown to yield kinases with reduced or absent catalytic activity.

Analysis of AAPK mutants and hybrid expression DNA constructs for ABA-activated protein kinase activity. $1.5 \times 10^7$ *V. faba* guard cell protoplasts were transfected with either the vector, pGFP, or the constructs, pAAPK-GFP or pAAPK(K43A)-GFP by polyethylene glycol (PEG)-mediated DNA transfer. After uptake and expression, protoplasts were lysed and recombinant protein was immunoprecipitated with anti-GFP peptide antibodies (Clontech) and protein A-Sepharose CL-4B (Amersham Pharmacia Biotech). Immunoprecipitated proteins were assayed for kinase activity using histone III-S (Sigma) as substrate.

Analysis of AAPK mutants for stomatal aperture changes and anion channel activation. *V. faba* leaves were biolistically transformed with the pGFP, pAAPK-GFP, or pAAPK (K43A)-GFP constructs. The *V. faba* leaves were bombarded with gold particles (Bio-Rad) coated with one of the DNA constructs. Bombardment was via a particle delivery system 1000/He (Bio-Rad) as described. (J. Marc et al., 1998, Plant Cell 10:1927).

Abaxial epidermal peels were isolated and the transformed guard cells were assayed for ABA-mediated prevention of stomatal opening and for stomatal closure stimulated by ABA, $CO_2$ or darkness. Conditions were as in Assman, S., and Baskin, T. (1998) J. Exp. Bot. 49:163 except that the incubation solution was 10 mM MES, 30 mM KCl, pH=6.1, with or without 50 μM {±} cis,trans-ABA. For closure experiments, the transformed leaves were illuminated with 0.20 mmol m$^{-2}$ s$^{-1}$ white light for 2.5 h to open the stomata. The abaxial epidermal peels were placed in incubation solution and treated with either darkness, 25 μM {±} cis, trans-ABA or with 700 ppm $CO_2$ for 1 h.

Anion channel activation was measured in guard cell protoplasts. Whole-cell patch-clamp experiments were performed according to established methods. Pipette solution contained 100 mM KCl, 50 mM tetramethylammonium, 2 mM MgCl, 6.7 mM EGTA-(Tris)$_2$, 3.35 mM CaCl$_2$, 10 mM HEPES, pH=7.1 (Tris) and 5 mM Mg-ATP. Bath solution contained 40 mM CaCl$_2$, 2 mM MgCl and 10 mM MES-Tris pH5.6. Osmolalities were adjusted with sorbitol to 500 mosmol/kg (in the pipette) or 470 mosmol/kg (in the bath). Protein kinase inhibitor K-252a (Calbiochem) was prepared as a stock solution at 2 mM in dimethyl sulfoxide (DMSO).

Results and Discussion

The *Vicia faba* ABA-Activated Protein Kinase (AAPK) is a 48 kDa protein. AAPK was identified as a 48 kDa ABA-dependent and Ca$^{2+}$-independent autophosphorylation spot with the in-gel kinase assay. The peptide fragment sequence information obtained is provided in FIG. 1. Two sequenced AAPK peptides had similarity to the protein kinase ABA1 (PKABA1) protein kinase subfamily in subdomains I and VIb. PKABA1 is transcriptionally up-regulated by ABA.

Cloning of a guard-cell-specific AAPK gene encoding ABA-Activated Protein Kinase (AAPK). The RT-PCR of total guard cell RNA using the degenerate primers yielded a 310 base pair sequence which encoded the peptides sequences from the AAPK and also encoded a sequence similar to that of the PKABA1 subfamily from subdomains II to VIb. A full length cDNA of the appropriate size to encode the AAPK was obtained from the screening of the *V. faba* cDNA library with this probe.

The nucleotide sequence of the full length AAPK cDNA and the amino acid sequence of the deduced AAPK protein are given in FIG. 1. The deduced AAPK amino acid sequence shows the greatest homology to the PKABAI subfamily. However, the predicted sequence also has unique regions.

Northern analysis showed that AAPK mRNA is expressed in guard cell protoplasts but not in mesophyll cell protoplasts, flowers, leaves, or seeds; true to the pattern of guard cell-specificity previously observed for AAPK activity. AAPK appears to be a single copy gene based on results from Southern analysis; however, further analysis may reveal the presence of more than one copy.

The in situ activation requirement for AAPK activity could be an indication that an intact cellular signal or cascade is required. Any discussion or explanation offered here is intended to provide clarity and is not intended to limit the invention in any way to one theory or avenue as to the mechanism or application.

ABA-dependent autophosphorylation and ABA-activated substrate phosphorylation. No histone phosphorylation was observed by the proteins immunoprecipitated from guard cells transformed with the control vector (pGFP) only. Phosphorylation activity of the fusion proteins AAPK-GFP and AAPK(K43A)-GFP was also determined. The immunoprecipitate from cells transfected with pAAPK-GFP showed histone phosphorylation activity which was significantly enhanced when the protoplasts were treated with ABA prior to isolation of the proteins. The fusion product of pAAPK-GFP showed both ABA-dependent autophosphorylation and the ABA-activated histone phophorylation, establishing that the cloned gene indeed encodes the observed biochemical activity of AAPK. The immunoprecipitate from cells transfected with pAAPK(K43A)-GFP, encoding the site-mutagenized AAPK(K43A), also showed ABA-dependent autophosphorylation and ABA-activated histone phosphorylation activity, however the relative levels were significantly reduced as would be predicted from the sequence change.

ABA-mediated stomatal aperture regulation and anion channel activation in AAPK mutants. The transformed guard cells were identified by their green fluorescence. Transformation with pAAPK(K43A)-GFP eliminated ABA-induced stomatal closure, but had no effect on stomatal closure induced by CO$_2$ or darkness. Transformation with wild-type AAPK via the pAAPK-GFP vector had no measurable effect on either ABA-induced stomatal closure nor on ABA-inhibition of stomatal opening.

In *V. faba* guard cells, ABA activated slow anion channels. Slow anion currents were identified by their characteristic time dependence, their reversal potential and sensitivity to the anion channel blocker 5-nitro-2-(3-phenylpropylamino) benzoic acid. Not only was the typical decay in anion current reversed over time in the whole-cell configuration, but ABA also increased the anion current magnitude. In guard cells transformed with pGFP or pAAPK-GFP, anion currents were regulated normally (activated) by ABA. In guard cells transformed with pAAPK(K43A)-GFP, however, ABA-activation of anion channels was eliminated.

It is likely that the K43A mutant kinase competes with the activity of native AAPK in a dominant negative fashion. First, the kinase inhibitor K-252a inhibits (i) native AAPK activity, (ii) ABA-induced stomatal closure, and (iii) ABA regulation of anion channels in untransformed cells, implying that the channels are indeed normally regulated by AAPK. Second, although dominant abi1-1 and abi2-1 mutations in ABI and ABI2 phosphatases confer ABA insensitivity to both anion channel activation and stomatal closure, recently identified recessive loss-of-function mutations in ABI1 confer hypersensitivity to ABA. Thus, in wild-type plants an AAPK may mediate ABA-induced anion channel activation and stomatal closure through a phosphorylation event, while ABI1 opposes ABA action through a dephosphorylation event.

Neither wild-type nor mutant versions of recombinant AAPK affected ABA inhibition of stomatal opening (Table 1). ABA inhibition of stomatal opening and ABA promotion of stomatal closure may, therefore, employ different signaling cascades. Alternatively, and in contrast to current theory, ABA activation of anion channels may not be required for ABA inhibition of stomatal opening.

Agronomically, loss of ABA-stimulated stomatal closure in plants transformed with mutant AAPK under control of an inducible promoter should allow accelerated and controlled desiccation of crops that are dried before harvest or distribution. Basal levels of ABA remain even in irrigated crops; under these conditions, inhibition of AAPK activity should alleviate stomatal limitation of CO$_2$ uptake, and thus accelerate growth or increase yield.

TABLE 1

Overexpression of AAPK(K43A) in guard cells inhibits ABA-induced stomatal closure. *V. faba* leaves were transformed and stomatal responses measured. ABA treatment was 25 μM (for closure) or 50 μM (for opening) (±)-cis, trans-ABA, elevated $CO_2$ treatment was 700 ppm $CO_2$. Except for the darkness treatment, peels were illuminated (0.20 mmol $m^{-2}s^{-1}$ white light) for the duration of each treatment. All numbers represent the change in half aperture of stomata as measured in micrometers. ND, not determined. Numbers in parentheses indicate sample sizes.

| | GFP | | AAPK-GFP | | AAPK (K43A)-GFP | |
|---|---|---|---|---|---|---|
| | Transformed | Untransformed | Transformed | Untransformed | Transformed | Untransformed |
| | | | Closure | | | |
| ABA | −2.52 ± 0.29 (36) | −2.54 ± 0.35 (36) | −2.59 ± 0.30 (36) | −2.58 ± 0.24 (36) | −0.36 ± 0.26 (56)* | −2.55 ± 0.21 (56) |
| Control | 0.10 ± 0.09 (10) | 0.09 ± 0.09 (10) | 0.11 ± 0.10 (10) | 0.12 ± 0.10 (24) | 0.12 ± 0.11 (10) | 0.13 ± 0.10 (24) |
| $CO_2$ | ND | ND | ND | ND | −2.23 ± 0.44 (36) | −2.31 ± 0.46 (36) |
| Control | | | | | −0.09 ± 0.09 (10) | −0.11 ± 0.10 (10) |
| Darkness | ND | ND | ND | ND | −2.08 ± 0.40 (36) | −2.08 ± 0.46 (36) |
| Control | | | | | 0.12 ± 0.11 (10) | 0.13 ± 0.11 (10) |
| | | | Opening | | | |
| ABA | 0.42 ± 0.22 (36) | 0.45 ± 0.27 (36) | 0.43 ± 0.22 (36) | 0.41 ± 0.28 (36) | 0.42 ± 0.17 (46) | 0.44 ± 0.15 (46) |

*Significantly different from untransformed cells treated with ABA (P < 0.001, Student's t test). Not significantly different from the AAPK(K43A)-GFP transformed ABA control (P > 0.05, Student's t test).

EXAMPLE 2

Identification of AAPK Genes from *Arabidopsis thaliana*

Screening. Standard methods known to those skilled in the art for screening a genomic library were used. An *Arabidopsis* genomic library from CD4-8 *Landsberg erecta* from the *Arabidopsis* Biological Resource Center at Ohio State University was used.

The probe was the Nco I-Bgl II fragment (393 base pairs) of *V. faba* AAPK cDNA. The gel-purified Nco I-Bgl II fragment of AAPK cDNA was labeled by 32P-dCTP. This probe corresponds to sequences encoding the region from the aspartic acid residue (position 2, SEQ ID NO:2) to the arginine residue (position 132, SEQ ID NO:2) of the AAPK protein.

Nylon membranes containing the library were prehybridized with 5×SSC, 5× Denhardt's solution, 1% SDS, and 0.2% nonfat milk at 60 C for 2 hours and then hybridized in the same solution with the labeled probe at 60 C overnight. The membranes were washed with 2×SSC and 0.1% SDS twice for 15 minutes at 60 C, once in 2×SSC and 0.1% SDS, and once in 0.5×SSC and 0.1% SDS. The membranes were exposed to X-ray films and positive plaques were identified by autoradiography.

The positive clones were subcloned into pCR BlueScript vector and then analyzed by DNA sequencing and compared to known sequences to look for matches.

Data Mining. The BLAST program of the National Center for Biological Information (NCBI) was used with the blastx option to search the nr (nonredundant) databases of GenBank, EMBL and DDBJ for matches with AAPK sequence data. The parameters used for the search were: expect value, 10; matrix, BLOSUM62; filter, low complexity.

Results. Two independent genomic clones were identified from the screening of the *Arabidopsis* library. Sequencing and subsequent database searches established that these sequences originated from sequences embodied respectively in GenBank Accession Numbers L05562 and Protein Identification Accession Number CAA19877. The data mining with the AAPK cDNA sequence corroborated the results obtained through screening of the genomic library. In addition, the database search revealed another, equally homologous, *Arabidopsis* nucleic acid sequence, comprising the sequences embodied in GenBank Accession Number L05561. The L05561 sequences correspond to a region within the *Arabidopsis* BAC clone ALO31032 of chromosome 4.

Sequence comparisons revealed that the predicted polypeptide encoded by L05562 has 75.4% identity with the amino acid sequence encoded by the *V. faba* AAPK cDNA, and the nucleotide sequence has 67.9% identity to the nucleotide sequence of the *V. faba* AAPK cDNA. The predicted polypeptide encoded by CAA19877 has 77.5% identity with the deduced *V. faba* AAPK amino acid sequence, and the nucleotide sequence is 68.7% identical to the nucleic acid sequence of *V. faba* AAPK cDNA. Various alignments and additional information regarding sequence identity are set forth in FIGS. 2–4.

The present invention is not limited to the embodiments described and exemplified above, but is capable of variation and modification without departure from the scope of the appended claims.

---

We claim:

1. An isolated nucleic acid molecule comprising a coding sequence encoding a polypeptide having protein kinase activity, comprising an amino acid sequence at least 95% identical to that of SEQ ID NO:2.

2. The nucleic acid molecule of claim 1, which is a cDNA.

3. The nucleic acid molecule of claim 1, which is genomic DNA comprising exons that form an open reading frame encoding the polypeptide.

4. The nucleic acid molecule of claim 1, which encodes a polypeptide having SEQ ID NO:2.

5. The nucleic acid molecule of claim 1, encoding a polypeptide wherein a lysine at position 43 of SEQ ID NO:2 is replaced with an alanine.

6. The nucleic acid molecule of claim 1, wherein the coding sequence is SEQ ID NO:1.

7. A vector for transforming a plant cell, comprising the nucleic acid molecule of claim 1.

8. A transformed plant cell comprising the vector of claim 7.

9. The nucleic acid molecule of claim 1, comprising a coding sequence at least 95% identical to the coding sequence of SEQ ID NO 1.

10. The vector of claim 7, which further comprises transcription or translation regulatory elements operably linked to the coding sequence, which enable expression of the coding sequence specifically in guard cells.

* * * * *

UNITED STATES PATENT AND TRADEMARK OFFICE
CERTIFICATE OF CORRECTION

| | | |
|---|---|---|
| PATENT NO. | : 7,211,436 B1 | Page 1 of 1 |
| APPLICATION NO. | : 09/606736 | |
| DATED | : May 1, 2007 | |
| INVENTOR(S) | : Sarah M. Assmann et al. | |

It is certified that error appears in the above-identified patent and that said Letters Patent is hereby corrected as shown below:

Title Page,
Item (56) References Cited
OTHER PUBLICATIONS:
"Lee, S.H., Lee M.H., Chung, W.I. and Liu, J.R." reference, after
"Genet. 1998." insert -- 259:516-522. USA. --.

Column 1,
Line 66, delete "phopsphorylation" and insert -- phosphorylation --.

Column 3,
Lines 46-47, delete "Koornneefet al. 1982," and insert -- Koornneef et al. 1982, --.

Column 4,
Line 35, delete "plants's" and insert -- plants' --.

Column 11,
Line 48, after "6" insert -- . --.

Column 13,
Line 67, delete "formamide)-600#bp in duplex" and insert -- formamide)-600/#bp in duplex --.

Column 14,
Line 28, delete "such a" and insert -- such as --.

Column 16,
Line 40, after "(An, 1986)" insert -- . --.

Signed and Sealed this

Twenty-second Day of July, 2008

JON W. DUDAS
*Director of the United States Patent and Trademark Office*

SEQUENCE LISTING

<160> NUMBER OF SEQ ID NOS: 20

<210> SEQ ID NO 1
<211> LENGTH: 1559
<212> TYPE: DNA
<213> ORGANISM: Vicia faba

```
<400> SEQUENCE: 1
cggcacgaga ttaaaaaggc cacaatgttg cttactctcc aacaacaacc gtaatcctct       60
cggaatctcc actacgacgc cgtttacttc cgatctctct ccccgccgga gcagcagcca      120
tggatatgcc gccgccgatc atgcacgaca gtgaccgtta cgacttcgtt cgtgatatcg      180
gatcgggaaa tttcggcgtc gctagactca tgactgataa actcaccaaa gaccttgttg      240
ctgtcaagta catcgaacgt ggagataaga ttgatgaaaa tgttaagaga gaaataatca      300
atcacaggtc tctaagacat cctaatattg ttaggtttaa ggaggtcatt ttaacaccta      360
ctcatctggc cattgtaatg gaatatgcat ctggaggaga aatgtccgat cgaatcagca      420
aagcggggcg ttttactgag gatgaggctc gtttcttctt tcaacaactc atatccgggg      480
tcagctattg tcattcaatg caagtatgtc atcgagatct gaagttggaa aacacgttgt      540
tggatggaga cccagcactt catctgaaga tttgtgattt tggatactcc aaatcttcgg      600
tgcttcattc acagccaaag tcaactgtgg gaactcctgc ttatattgct ccagaagtac      660
ttctgaagca agagtatgat ggaaagattg ccgatgtctg gtcatgtggt gtaaccttat      720
acgtgatgct agtggggtca tatccttttg aagatcccga taatccgaag gatttccgga      780
agacaattca gagggttctc agtgtccagt attccgtacc agactttgtt caaatatctc      840
ctgaatgtcg cgacattata tcaagaatct tgttttttga ccctgcagag gaatcacca       900 ttccagaaat aatgaagaac gaatggttcc gaaagaatct tcctgctgac ttggtgaatg      960
aaaatataat ggataaccaa tttgaagagc cagatcagcc tatgcagagt atggatacga     1020
tcatgcagat aatttcagaa gctaccgtac cagcagctgg gagctattat tttgacgagt     1080
ttatcgaagt ggatgaagat atggatgaaa tagactctga ctatgaactt gatgtagata     1140
gcagtggtga gattgtatat gccatataat ttaatcatca tagaggtcac atattgaaaa     1200
ggaagcacct tatattgagc tttatggctt tctcagcctc aaagctaaaa aaataaaatat     1260 tctgagacta ttttctgcag actggatgat gcacgaagtt catcatgttg atttatatat     1320
tgtatgcttt cttggaacat gcattgtcca ccacatttat aagtatcact tttgtgagtt     1380
gaggcaacat gttttcgaat ttgtagggat cttctttatt ccttaaaaaa agttccacaa     1440
cttcaattta ggatgtatat tggcataatt ttagaacgtg gcatggcata attgagattt     1500
tatatgcatg aaatatggta acgagctctt gatttctttt caaaaaaaaa aaaaaaaa      1559
```

<210> SEQ ID NO 2
<211> LENGTH: 349
<212> TYPE: PRT
<213> ORGANISM: Vicia faba

<400> SEQUENCE: 2

```
Met Asp Met Pro Pro Pro Ile Met His Asp Ser Asp Arg Tyr Asp Phe
 1               5                  10                  15

Val Arg Asp Ile Gly Ser Gly Asn Phe Gly Val Ala Arg Leu Met Thr
            20                  25                  30

Asp Lys Leu Thr Lys Asp Leu Val Ala Val Lys Tyr Ile Glu Arg Gly
        35                  40                  45

Asp Lys Ile Asp Glu Asn Val Lys Arg Glu Ile Ile Asn His Arg Ser
    50                  55                  60

Leu Arg His Pro Asn Ile Val Arg Phe Lys Glu Val Ile Leu Thr Pro
65                  70                  75                  80

Thr His Leu Ala Ile Val Met Glu Tyr Ala Ser Gly Gly Glu Met Ser
                85                  90                  95
```

```
Asp Arg Ile Ser Lys Ala Gly Arg Phe Thr Glu Asp Glu Ala Arg Phe
            100                 105                 110
Phe Phe Gln Gln Leu Ile Ser Gly Val Ser Tyr Cys His Ser Met Gln
        115                 120                 125
Val Cys His Arg Asp Leu Lys Leu Glu Asn Thr Leu Leu Asp Gly Asp
    130                 135                 140
Pro Ala Leu His Leu Lys Ile Cys Asp Phe Gly Tyr Ser Lys Ser Ser
145                 150                 155                 160
Val Leu His Ser Gln Pro Lys Ser Thr Val Gly Thr Pro Ala Tyr Ile
                165                 170                 175
Ala Pro Glu Val Leu Leu Lys Gln Glu Tyr Asp Gly Lys Ile Ala Asp
            180                 185                 190
Val Trp Ser Cys Gly Val Thr Leu Tyr Val Met Leu Val Gly Ser Tyr
        195                 200                 205
Pro Phe Glu Asp Pro Asp Asn Pro Lys Asp Phe Arg Lys Thr Ile Gln
    210                 215                 220
Arg Val Leu Ser Val Gln Tyr Ser Val Pro Asp Phe Val Gln Ile Ser
225                 230                 235                 240
Pro Glu Cys Arg Asp Ile Ile Ser Arg Ile Phe Val Phe Asp Pro Ala
                245                 250                 255
Glu Arg Ile Thr Ile Pro Glu Ile Met Lys Asn Glu Trp Phe Arg Lys
            260                 265                 270
Asn Leu Pro Ala Asp Leu Val Asn Glu Asn Ile Met Asp Asn Gln Phe
        275                 280                 285
Glu Glu Pro Asp Gln Pro Met Gln Ser Met Asp Thr Ile Met Gln Ile
    290                 295                 300
Ile Ser Glu Ala Thr Val Pro Ala Ala Gly Ser Tyr Tyr Phe Asp Glu
305                 310                 315                 320
Phe Ile Glu Val Asp Glu Asp Met Asp Glu Ile Asp Ser Asp Tyr Glu
                325                 330                 335
Leu Asp Val Asp Ser Ser Gly Glu Ile Val Tyr Ala Ile
            340                 345

<210> SEQ ID NO 3
<211> LENGTH: 1454
<212> TYPE: DNA
<213> ORGANISM: Arabidopsis thaliana

<400> SEQUENCE: 3 ttttttttttt tttttccatt tatttctcg  aatcttcttc ttcttcctag attccagcga      60
cttaacaaca acaacaacaa catattctct gctgggtatt agattcgaat ttctcttttt     120
gtgatcagaa atggatcgag ctccggtgac cacaggaccg ttggatatgc cgattatgca     180
cgacagtgat cgatatgact tcgttaagga tattggttct ggtaatttcg gtgttgctcg     240
tcttatgaga gataaactca ctaaagagct tgttgctgtc aagtacatcg agagaggaga     300
caagattgat gaaaatgttc aaagggagat cattaaccac aggtcactaa ggcatcctaa     360
tattgtcaga tttaaagagg tcattttgac gccgactcat ctggctatca taatggaata     420
tgcttctggc ggtgaacttt acgagcggat ttgcaatgca ggacggttta gtgaagatga     480
ggctcggttc ttctttcagc agcttctatc tggagtcagt tattgtcatt cgatgcaaat     540
ttgccatcgt gacctgaagc tagagaatac attgttggat ggaagtcctg ctcctcgatt     600
aaaaatttgt gatttggat  attcaaagtc ttctgttctt cattcacaac caaagtcaac     660
```

-continued

```
tgttggtact cctgcataca tcgctccaga ggtactgctt cgtcaggaat atgatggcaa      720
gattgcagat gtatggtcat gtggtgtgac cttatacgtc atgttggttg gagcgtatcc      780
gttcgaagat ccagaagagc caagagacta tcggaaaaca atacagagaa tccttagcgt      840
taaatactca atccctgatg acatacggat atcacctgaa tgctgtcatc ttatttcaag      900
aatcttcgtg gctgatcccg ctaccagaat aagcatacca gagatcaaaa cccatagttg      960
gttcttgaag aatctccctg ctgatctaat gaacgagagc aacacaggaa gccagttcca     1020
ggagcctgaa caaccaatgc aaagccttga cacaatcatg caaatcatct ctgaagccac     1080
aattcccgct gttcgaaacc gttgcctaga cgatttcatg actgacaatc ttgatcttga     1140
cgatgacatg gatgactttg actctgaatc tgaaatcgac attgacagta gcggagagat     1200
agtttacgct ctctaataaa aagcttttt taacaaccaa aacacttctc tatctgttct     1260
aagaccagta gtgttctgat cctctggttt caaattctac caatttttgt attgtctctg     1320
tttgtttctt gttttcttca tgcacacata tatcatatat gtaatgtaaa atatcatctg     1380
tgtatattat atatatattc caatgtcaca caaaagcaaa ttaacagtta aaacagttga     1440
agcaagttga ggtt                                                       1454
```

<210> SEQ ID NO 4
<211> LENGTH: 361
<212> TYPE: PRT
<213> ORGANISM: Arabidopsis thaliana

<400> SEQUENCE: 4

```
Met Asp Arg Ala Pro Val Thr Thr Gly Pro Leu Asp Met Pro Ile Met
  1               5                  10                  15

His Asp Ser Asp Arg Tyr Asp Phe Val Lys Asp Ile Gly Ser Gly Asn
             20                  25                  30

Phe Gly Val Ala Arg Leu Met Arg Asp Lys Leu Thr Lys Glu Leu Val
         35                  40                  45

Ala Val Lys Tyr Ile Glu Arg Gly Asp Lys Ile Asp Glu Asn Val Gln
     50                  55                  60

Arg Glu Ile Ile Asn His Arg Ser Leu Arg His Pro Asn Ile Val Arg
 65                  70                  75                  80

Phe Lys Glu Val Ile Leu Thr Pro Thr His Leu Ala Ile Ile Met Glu
                 85                  90                  95

Tyr Ala Ser Gly Gly Glu Leu Tyr Glu Arg Ile Cys Asn Ala Gly Arg
            100                 105                 110

Phe Ser Glu Asp Glu Ala Arg Phe Phe Gln Gln Leu Leu Ser Gly
        115                 120                 125

Val Ser Tyr Cys His Ser Met Gln Ile Cys His Arg Asp Leu Lys Leu
    130                 135                 140

Glu Asn Thr Leu Leu Asp Gly Ser Pro Ala Pro Arg Leu Lys Ile Cys
145                 150                 155                 160

Asp Phe Gly Tyr Ser Lys Ser Ser Val Leu His Ser Gln Pro Lys Ser
                165                 170                 175

Thr Val Gly Thr Pro Ala Tyr Ile Ala Pro Glu Val Leu Leu Arg Gln
            180                 185                 190

Glu Tyr Asp Gly Lys Ile Ala Asp Val Trp Ser Cys Gly Val Thr Leu
        195                 200                 205

Tyr Val Met Leu Val Gly Ala Tyr Pro Phe Glu Asp Pro Glu Glu Pro
    210                 215                 220

Arg Asp Tyr Arg Lys Thr Ile Gln Arg Ile Leu Ser Val Lys Tyr Ser
```

```
                225                 230                 235                 240
Ile Pro Asp Asp Ile Arg Ile Ser Pro Glu Cys Cys His Leu Ile Ser
                    245                 250                 255
Arg Ile Phe Val Ala Asp Pro Ala Thr Arg Ile Ser Ile Pro Glu Ile
                260                 265                 270
Lys Thr His Ser Trp Phe Leu Lys Asn Leu Pro Ala Asp Leu Met Asn
                275                 280                 285
Glu Ser Asn Thr Gly Ser Gln Phe Gln Glu Pro Gln Pro Met Gln
    290                 295                 300
Ser Leu Asp Thr Ile Met Gln Ile Ile Ser Glu Ala Thr Ile Pro Ala
305                 310                 315                 320
Val Arg Asn Arg Cys Leu Asp Asp Phe Met Thr Asp Asn Leu Asp Leu
                325                 330                 335
Asp Asp Asp Met Asp Asp Phe Asp Ser Glu Ser Glu Ile Asp Ile Asp
                340                 345                 350
Ser Ser Gly Glu Ile Val Tyr Ala Leu
                355                 360

<210> SEQ ID NO 5
<211> LENGTH: 357
<212> TYPE: PRT
<213> ORGANISM: Arabidopsis thaliana

<400> SEQUENCE: 5

Met Asp Arg Pro Ala Val Ser Gly Pro Met Asp Leu Pro Ile Met His
1               5                   10                  15
Asp Ser Asp Arg Tyr Glu Leu Val Lys Asp Ile Gly Ser Gly Asn Phe
                20                  25                  30
Gly Val Ala Arg Leu Met Arg Asp Lys Gln Ser Asn Glu Leu Val Ala
            35                  40                  45
Val Lys Tyr Ile Glu Arg Gly Glu Lys Ile Asp Glu Asn Val Lys Arg
        50                  55                  60
Glu Ile Ile Asn His Arg Ser Leu Arg His Pro Asn Ile Val Arg Phe
65                  70                  75                  80
Lys Glu Val Ile Leu Thr Pro Thr His Leu Ala Ile Val Met Glu Tyr
                85                  90                  95
Ala Ser Gly Gly Glu Leu Phe Glu Arg Ile Cys Asn Ala Gly Arg Phe
            100                 105                 110
Ser Glu Asp Glu Ala Arg Phe Phe Gln Gln Leu Ile Ser Gly Val
        115                 120                 125
Ser Tyr Cys His Ala Met Gln Val Cys His Arg Asp Leu Lys Leu Glu
    130                 135                 140
Asn Thr Leu Leu Asp Gly Ser Pro Ala Pro Arg Leu Lys Ile Cys Asp
145                 150                 155                 160
Phe Gly Tyr Ser Lys Ser Ser Val Leu His Ser Gln Pro Lys Ser Thr
                165                 170                 175
Val Gly Thr Pro Ala Tyr Ile Ala Pro Glu Val Leu Leu Lys Lys Glu
            180                 185                 190
Tyr Asp Gly Lys Val Ala Asp Val Trp Ser Cys Gly Val Thr Leu Tyr
        195                 200                 205
Val Met Leu Val Gly Ala Tyr Pro Phe Glu Asp Pro Glu Glu Pro Lys
    210                 215                 220
Asn Phe Arg Lys Thr Ile His Arg Ile Leu Asn Val Gln Tyr Ala Ile
225                 230                 235                 240
```

```
Pro Asp Tyr Val His Ile Ser Pro Glu Cys Arg His Leu Ile Ser Arg
                245                 250                 255
Ile Phe Val Ala Asp Pro Ala Lys Arg Ile Ser Ile Pro Glu Ile Arg
            260                 265                 270
Asn His Glu Trp Phe Leu Lys Asn Leu Pro Ala Asp Leu Met Asn Asp
        275                 280                 285
Asn Thr Met Thr Thr Gln Phe Asp Glu Ser Asp Gln Pro Gly Gln Ser
    290                 295                 300
Ile Glu Glu Ile Met Gln Ile Ala Glu Ala Thr Val Pro Pro Ala
305                 310                 315                 320
Gly Thr Gln Asn Leu Asn His Tyr Leu Thr Asp Asp Met Glu Glu
                325                 330                 335
Asp Leu Glu Ser Asp Leu Asp Asp Leu Asp Ile Asp Ser Ser Gly Glu
            340                 345                 350
Ile Val Tyr Ala Met
        355
```

<210> SEQ ID NO 6
<211> LENGTH: 1448
<212> TYPE: DNA
<213> ORGANISM: Arabidopsis thaliana

<400> SEQUENCE: 6

```
ggaattccct ttttccccca aattcatatc cttccttaga tattttttctc cttcttcttc      60
ttctagattc cagctactcc agaagattct tcgacttaat ctgatgtgat taggaagagc     120
aatagaggaa gagaatcaga aaaaatggat ccggcgacta attcaccgat tatgccgatt     180
gatttaccga ttatgcacga cagtgatcgt tacgacttcg ttaaagatat tggctctggt     240
aatttcggcg ttgctcgtct catgaccgat agagtcacca aggagcttgt tgctgttaaa     300
tacatcgaga gaggagaaaa gattgatgaa aatgttcaga gggagattat caatcataga     360
tcattgagac atcctaatat tgttaggttt aaagaggtga ttttgacgcc ttcccatttg     420
gctattgtta tggaatatgc tgctggtgga aactttatg agcggatttg taatgccgga     480
cggtttagtg aagatgaggc tcggttcttc tttcagcagc ttatatctgg agttagctat     540
tgtcatgcaa tgcaaatatg ccatcgggat ctgaagctgg aaaatacatt gttagatgga     600
agtccggcac ctcgtttgaa aatatgtgat tttggttatt ccaagtcttc tgttcttcat     660
tcccaaccaa agtcaactgt tggtactcct gcatacattg caccagagat tcttcttcga     720
caggaatatg atggcaagct tgcagatgta tggtcttgcg gtgtaacatt atatgtaatg     780
ttggttggag cttatccatt cgaggatcca caggagccac gagattatcg aaagacaata     840
caaagaatcc ttagtgtcac atactcgatc ccagaggact acacctctc accagaatgt     900
cgccatctaa tatcgaggat cttcgtggct gatccggcaa caagaatcac tattccggag     960
atcacatccg ataaatggtt cttgaagaat ctaccaggtg atttgatgga tgagaaccga    1020
atgggaagtc agtttcaaga gcctgagcag ccaatgcaga gccttgacac gattatgcag    1080
ataatatcgg aggctacgat tccgactgtt cgtaatcgtt gcctcgatga tttcatggcg    1140
gataatcttg atctagacga tgacatggat gactttgatt ccgaatctga gattgatgtt    1200
gacagtagtg gagagatagt ttatgctctc tgagattcct gaggacaaag tctgttttgt    1260
ccgtactgtt gagacacacc actggagttt tgtcttagct ccacgcactc catcgttcat    1320
ttttggatcg tttgttgttt tttactctac aagctttgga ttcacataca tatatatgta    1380
ttgtaatgta atatgtaata tattctatgt atttctcttt gtttaataac tattggcaca    1440
```

```
tttttatac                                                         1448
```

<210> SEQ ID NO 7
<211> LENGTH: 362
<212> TYPE: PRT
<213> ORGANISM: Arabidopsis thaliana

<400> SEQUENCE: 7

```
Met Asp Pro Ala Thr Asn Ser Pro Ile Met Pro Ile Asp Leu Pro Ile
 1               5                  10                  15

Met His Asp Ser Asp Arg Tyr Asp Phe Val Lys Asp Ile Gly Ser Gly
            20                  25                  30

Asn Phe Gly Val Ala Arg Leu Met Thr Asp Arg Val Thr Lys Glu Leu
        35                  40                  45

Val Ala Val Lys Tyr Ile Glu Arg Gly Glu Lys Ile Asp Glu Asn Val
    50                  55                  60

Gln Arg Glu Ile Ile Asn His Arg Ser Leu Arg His Pro Asn Ile Val
65                  70                  75                  80

Arg Phe Lys Glu Val Ile Leu Thr Pro Ser His Leu Ala Ile Val Met
                85                  90                  95

Glu Tyr Ala Ala Gly Gly Glu Leu Tyr Glu Arg Ile Cys Asn Ala Gly
            100                 105                 110

Arg Phe Ser Glu Asp Glu Ala Arg Phe Phe Gln Gln Leu Ile Ser
        115                 120                 125

Gly Val Ser Tyr Cys His Ala Met Gln Ile Cys His Arg Asp Leu Lys
    130                 135                 140

Leu Glu Asn Thr Leu Leu Asp Gly Ser Pro Ala Pro Arg Leu Lys Ile
145                 150                 155                 160

Cys Asp Phe Gly Tyr Ser Lys Ser Ser Val Leu His Ser Gln Pro Lys
                165                 170                 175

Ser Thr Val Gly Thr Pro Ala Tyr Ile Ala Pro Glu Ile Leu Leu Arg
            180                 185                 190

Gln Glu Tyr Asp Gly Lys Leu Ala Asp Val Trp Ser Cys Gly Val Thr
        195                 200                 205

Leu Tyr Val Met Leu Val Gly Ala Tyr Pro Phe Glu Asp Pro Gln Glu
    210                 215                 220

Pro Arg Asp Tyr Arg Lys Thr Ile Gln Arg Ile Leu Ser Val Thr Tyr
225                 230                 235                 240

Ser Ile Pro Glu Asp Leu His Leu Ser Pro Glu Cys Arg His Leu Ile
                245                 250                 255

Ser Arg Ile Phe Val Ala Asp Pro Ala Thr Arg Ile Thr Ile Pro Glu
            260                 265                 270

Ile Thr Ser Asp Lys Trp Phe Leu Lys Asn Leu Pro Gly Asp Leu Met
    275                 280                 285

Asp Glu Asn Arg Met Gly Ser Gln Phe Gln Glu Pro Glu Gln Pro Met
290                 295                 300

Gln Ser Leu Asp Thr Ile Met Gln Ile Ile Ser Glu Ala Thr Ile Pro
305                 310                 315                 320

Thr Val Arg Asn Arg Cys Leu Asp Asp Phe Met Ala Asp Asn Leu Asp
                325                 330                 335

Leu Asp Asp Asp Met Asp Asp Phe Asp Ser Glu Ser Glu Ile Asp Val
            340                 345                 350

Asp Ser Ser Gly Glu Ile Val Tyr Ala Leu
        355                 360
```

<210> SEQ ID NO 8
<211> LENGTH: 362
<212> TYPE: PRT
<213> ORGANISM: Arabidopsis thaliana

<400> SEQUENCE: 8

```
Met Asp Pro Ala Thr Asn Ser Pro Ile Met Pro Ile Asp Leu Pro Ile
 1               5                  10                  15

Met His Asp Ser Asp Arg Tyr Asp Phe Val Lys Asp Ile Gly Ser Gly
            20                  25                  30

Asn Phe Gly Val Ala Arg Leu Met Thr Asp Arg Val Thr Lys Glu Leu
        35                  40                  45

Val Ala Val Lys Tyr Ile Glu Arg Gly Glu Lys Ile Asp Glu Asn Val
    50                  55                  60

Gln Arg Glu Ile Ile Asn His Arg Ser Leu Arg His Pro Asn Ile Val
 65                  70                  75                  80

Arg Phe Lys Glu Val Ile Leu Thr Pro Ser His Leu Ala Ile Val Met
                 85                  90                  95

Glu Tyr Ala Ala Gly Gly Glu Leu Tyr Glu Arg Ile Cys Asn Ala Gly
            100                 105                 110

Arg Phe Ser Glu Asp Glu Ala Arg Phe Phe Phe Gln Gln Leu Ile Ser
        115                 120                 125

Gly Val Ser Tyr Cys His Ala Met Gln Ile Cys His Arg Asp Leu Lys
    130                 135                 140

Leu Glu Asn Thr Leu Leu Asp Gly Ser Pro Ala Pro Arg Leu Lys Ile
145                 150                 155                 160

Cys Asp Phe Gly Tyr Ser Lys Ser Ser Val Leu His Ser Gln Pro Lys
                165                 170                 175

Ser Thr Val Gly Thr Pro Ala Tyr Ile Ala Pro Glu Ile Leu Leu Arg
            180                 185                 190

Gln Glu Tyr Asp Gly Lys Leu Ala Asp Val Trp Ser Cys Gly Val Thr
        195                 200                 205

Leu Tyr Val Met Leu Val Gly Ala Tyr Pro Phe Glu Asp Pro Gln Glu
    210                 215                 220

Pro Arg Asp Tyr Arg Lys Thr Ile Gln Arg Ile Leu Ser Val Thr Tyr
225                 230                 235                 240

Ser Ile Pro Glu Asp Leu His Leu Ser Pro Glu Cys Arg His Leu Ile
                245                 250                 255

Ser Arg Ile Phe Val Ala Asp Pro Ala Thr Arg Ile Thr Ile Pro Glu
            260                 265                 270

Ile Thr Ser Asp Lys Trp Phe Leu Lys Asn Leu Pro Gly Asp Leu Met
        275                 280                 285

Asp Glu Asn Arg Met Gly Ser Gln Phe Gln Glu Pro Glu Gln Pro Met
    290                 295                 300

Gln Ser Leu Asp Thr Ile Met Gln Ile Ile Ser Glu Ala Thr Ile Pro
305                 310                 315                 320

Thr Val Arg Asn Arg Cys Leu Asp Asp Phe Met Ala Asp Asn Leu Asp
                325                 330                 335

Leu Asp Asp Asp Met Asp Asp Phe Asp Ser Glu Ser Glu Ile Asp Val
            340                 345                 350

Asp Ser Ser Gly Glu Ile Val Tyr Ala Leu
        355                 360
```

<210> SEQ ID NO 9
<211> LENGTH: 1210
<212> TYPE: DNA
<213> ORGANISM: Triticum aestivum

<400> SEQUENCE: 9

| | | | | | |
|---|---|---|---|---|---|
| ggttccggca | acttcggggt | ggccaagctg | gtgcgggacg | tccggaccaa | ggagcacttc | 60 |
| gccgtcaagt | tcatcgagcg | aggccacaag | attgatgaac | atgttcaaag | ggagattatg | 120 |
| aaccaccggt | cactcaagca | tccaaatatt | attcgattca | aggaggtcgt | gctaactccc | 180 |
| acacatttgg | caatagttat | ggaatatgcc | tctggcggcg | agctatttca | aggatttgc | 240 |
| aacgcaggga | gatttagcga | ggatgaggga | agattcttct | tccaacaatt | gatttctgga | 300 |
| gtgagctatt | gtcactctat | gcaagtatgt | catagagatt | tgaaactaga | aaacactctc | 360 |
| ttggatggta | gtgtcgcacc | tcggctcaag | atttgtgact | tcggttactc | caagtcttct | 420 |
| gtcttgcact | ctcaaccgaa | gtcaactgtc | ggcacaccgg | catacatcgc | cccagaggtc | 480 |
| ctctctagaa | gagaatatga | tggaaaggtc | gccgatgttt | ggtcatgcgg | agtaacgctc | 540 |
| tatgtgatgc | ttgtcggggc | atatcctttc | gaggaccctg | atgagccaag | gaacttccgc | 600 |
| aaaacgatca | ctaggatact | cagcgtacag | tactctgttc | cggactacgt | tcgagtctcg | 660 |
| atggactgca | tacatctact | gtcccgcatt | ttcgttggaa | atcctcagca | gcgaataacc | 720 |
| atcccggaga | tcaagaacca | tccatggttc | ctcaagagat | tgcccgttga | gatgaccgat | 780 |
| gagtaccaaa | ggagcatgca | gctggcagac | atgaacacgc | cgtcacagag | cctggaagaa | 840 |
| gccatggcga | tcatccagga | ggcgcagaaa | cctggcgata | acgccctagg | ggttgccggg | 900 |
| caggttgcct | gcctggggag | catggatttg | gacgacatcg | atttcgatat | cgacgacatt | 960 |
| gacgttgaga | gcagcgggga | tttcgtgtgc | ccgttgtgat | tgctcatgag | tggttcaaaa | 1020 |
| gttctcttga | tggtttgcct | gtggatggat | ccctgttttg | tcatgcttcc | actagatttt | 1080 |
| gttctgggtc | acaaattctc | tgtagcctac | agattggctt | gatgtgtaaa | cagtgtaaga | 1140 |
| taagtttaca | tgcttatatc | gaaatcagta | gttttacccg | aaaaaaaaaa | aaaaaaaaa | 1200 |
| aaaaaaaaaa | | | | | | 1210 |

<210> SEQ ID NO 10
<211> LENGTH: 332
<212> TYPE: PRT
<213> ORGANISM: Triticum aestivum

<400> SEQUENCE: 10

Gly Ser Gly Asn Phe Gly Val Ala Lys Leu Val Arg Asp Val Arg Thr
 1               5                  10                  15

Lys Glu His Phe Ala Val Lys Phe Ile Glu Arg Gly His Lys Ile Asp
            20                  25                  30

Glu His Val Gln Arg Glu Ile Met Asn His Arg Ser Leu Lys His Pro
        35                  40                  45

Asn Ile Ile Arg Phe Lys Glu Val Val Leu Thr Pro Thr His Leu Ala
    50                  55                  60

Ile Val Met Glu Tyr Ala Ser Gly Gly Glu Leu Phe Gln Arg Ile Cys
65                  70                  75                  80

Asn Ala Gly Arg Phe Ser Glu Asp Glu Gly Arg Phe Phe Gln Gln
            85                  90                  95

Leu Ile Ser Gly Val Ser Tyr Cys His Ser Met Gln Val Cys His Arg
           100                 105                 110

Asp Leu Lys Leu Glu Asn Thr Leu Leu Asp Gly Ser Val Ala Pro Arg

-continued

```
                115                 120                 125
Leu Lys Ile Cys Asp Phe Gly Tyr Ser Lys Ser Val Leu His Ser
    130                 135                 140

Gln Pro Lys Ser Thr Val Gly Thr Pro Ala Tyr Ile Ala Pro Glu Val
145                 150                 155                 160

Leu Ser Arg Arg Glu Tyr Asp Gly Lys Val Ala Asp Val Trp Ser Cys
                165                 170                 175

Gly Val Thr Leu Tyr Val Met Leu Val Gly Ala Tyr Pro Phe Glu Asp
            180                 185                 190

Pro Asp Glu Pro Arg Asn Phe Arg Lys Thr Ile Thr Arg Ile Leu Ser
        195                 200                 205

Val Gln Tyr Ser Val Pro Asp Tyr Val Arg Val Ser Met Asp Cys Ile
    210                 215                 220

His Leu Leu Ser Arg Ile Phe Val Gly Asn Pro Gln Gln Arg Ile Thr
225                 230                 235                 240

Ile Pro Glu Ile Lys Asn His Pro Trp Phe Leu Lys Arg Leu Pro Val
                245                 250                 255

Glu Met Thr Asp Glu Tyr Gln Arg Ser Met Gln Leu Ala Asp Met Asn
            260                 265                 270

Thr Pro Ser Gln Ser Leu Glu Glu Ala Met Ala Ile Ile Gln Glu Ala
        275                 280                 285

Gln Lys Pro Gly Asp Asn Ala Leu Gly Val Ala Gly Gln Val Ala Cys
    290                 295                 300

Leu Gly Ser Met Asp Leu Asp Asp Ile Asp Phe Asp Ile Asp Asp Ile
305                 310                 315                 320

Asp Val Glu Ser Ser Gly Asp Phe Val Cys Pro Leu
                325                 330

<210> SEQ ID NO 11
<211> LENGTH: 339
<212> TYPE: PRT
<213> ORGANISM: Nicotiana tabacum

<400> SEQUENCE: 11

Met Glu Glu Lys Tyr Glu Leu Leu Lys Glu Leu Gly Thr Gly Asn Phe
1               5                   10                  15

Gly Val Ala Arg Leu Val Lys Asp Lys Thr Lys Glu Leu Phe Ala
            20                  25                  30

Val Lys Tyr Ile Glu Arg Gly Lys Lys Ile Asp Glu Asn Val Gln Arg
        35                  40                  45

Glu Ile Ile Asn His Arg Ser Leu Gly His Pro Asn Ile Ile Arg Phe
    50                  55                  60

Lys Glu Val Leu Val Thr Pro Ser His Leu Ala Ile Val Met Glu Tyr
65                  70                  75                  80

Ala Ala Gly Gly Glu Leu Phe Ala Arg Ile Cys Ser Ala Gly Arg Phe
                85                  90                  95

Ser Glu Asp Glu Ala Arg Phe Phe Gln Gln Leu Ile Ser Gly Val
            100                 105                 110

Ser Tyr Cys His Ala Met Glu Ile Cys His Arg Asp Leu Lys Leu Glu
    115                 120                 125

Asn Thr Leu Leu Asp Gly Ser Ala Ser Pro Arg Val Lys Ile Cys Asp
    130                 135                 140

Phe Gly Tyr Ser Lys Ser Gly Leu Leu His Ser Gln Pro Lys Ser Thr
145                 150                 155                 160
```

```
Val Gly Thr Pro Ala Tyr Ile Ala Pro Glu Val Leu Ser Arg Lys Glu
                165                 170                 175

Tyr Asp Gly Lys Ile Ala Asp Val Trp Ser Cys Gly Val Thr Leu Tyr
            180                 185                 190

Val Met Leu Val Gly Ala Tyr Pro Phe Glu Asp Pro Glu Asp Pro Lys
        195                 200                 205

Asn Phe Arg Lys Thr Ile Gly Arg Ile Met Ser Ala Gln Tyr Ser Ile
    210                 215                 220

Pro Asp Tyr Val Arg Ile Ser Ala Asp Cys Lys Asn Leu Leu Ser Arg
225                 230                 235                 240

Ile Phe Val Ala Asn Pro Ser Lys Arg Ile Thr Ile Pro Glu Ile Lys
                245                 250                 255

Lys His Pro Trp Phe Leu Lys Asn Leu Pro Lys Asp Leu Met Asp Gly
            260                 265                 270

Glu His Ser Lys Tyr Glu Glu Ala Ser Glu Gln Leu Gln Gln Ser Val
        275                 280                 285

Glu Glu Ile Met Arg Ile Ile Gln Glu Ala Lys Ile Pro Gly Glu Val
    290                 295                 300

Ser Lys Pro Glu Gly Gln Ala Thr Ala Gly Thr Ala Glu Pro Asp Asp
305                 310                 315                 320

Thr Glu Asp Asp Leu Glu Ser Glu Ile Asp Ser Ser Asn Asp Phe Ala
                325                 330                 335

Val Tyr Val

<210> SEQ ID NO 12
<211> LENGTH: 349
<212> TYPE: PRT
<213> ORGANISM: Glycine max

<400> SEQUENCE: 12

Met Asp Lys Tyr Glu Ala Val Lys Asp Leu Gly Ala Gly Asn Phe Gly
  1               5                  10                  15

Val Ala Arg Leu Met Arg Asn Lys Val Thr Lys Glu Leu Val Ala Met
            20                  25                  30

Lys Tyr Ile Glu Arg Gly Pro Lys Ile Asp Glu Asn Val Ala Arg Glu
        35                  40                  45

Ile Met Asn His Arg Ser Leu Arg His Pro Asn Ile Ile Arg Tyr Lys
    50                  55                  60

Glu Val Val Leu Thr Pro Thr His Leu Ala Ile Val Met Glu Tyr Ala
65                  70                  75                  80

Ala Gly Gly Glu Leu Phe Glu Arg Ile Cys Ser Ala Gly Arg Phe Ser
                85                  90                  95

Glu Asp Glu Ala Arg Tyr Phe Phe Gln Gln Leu Ile Ser Gly Val His
            100                 105                 110

Phe Cys His Thr Met Gln Ile Cys His Arg Asp Leu Lys Leu Glu Asn
        115                 120                 125

Thr Leu Leu Asp Gly Ser Pro Ala Pro Arg Leu Lys Ile Cys Asp Phe
    130                 135                 140

Gly Tyr Ser Lys Ser Ser Leu Leu His Ser Arg Pro Lys Ser Thr Val
145                 150                 155                 160

Gly Thr Pro Ala Tyr Ile Ala Pro Glu Val Leu Ser Arg Arg Glu Tyr
                165                 170                 175

Asp Gly Lys Leu Ala Asp Val Trp Ser Cys Ala Val Thr Leu Tyr Val
            180                 185                 190
```

```
Met Leu Val Gly Ala Tyr Pro Phe Glu Asp Gln Asp Pro Arg Asn
            195                 200                 205

Phe Arg Lys Thr Ile Gln Arg Ile Met Ala Val Gln Tyr Lys Ile Pro
210                 215                 220

Asp Tyr Val His Ile Ser Gln Asp Cys Arg His Leu Leu Ser Arg Ile
225                 230                 235                 240

Phe Val Ala Asn Pro Leu Arg Arg Ile Thr Ile Lys Glu Ile Lys Asn
                245                 250                 255

His Pro Trp Phe Leu Arg Asn Leu Pro Arg Glu Leu Thr Glu Ser Ala
            260                 265                 270

Gln Ala Ile Tyr Tyr Gln Arg Asp Ser Pro Asn Phe His Leu Gln Ser
        275                 280                 285

Val Asp Glu Ile Met Lys Ile Val Gly Glu Ala Arg Asn Pro Pro Pro
    290                 295                 300

Val Ser Arg Ala Leu Lys Gly Phe Gly Trp Glu Gly Glu Glu Asp Leu
305                 310                 315                 320

Asp Glu Glu Val Glu Glu Glu Asp Glu Asp Glu Tyr Asp Lys Arg
                325                 330                 335

Val Lys Glu Val His Ala Ser Gly Glu Phe Gln Ile Ser
            340                 345

<210> SEQ ID NO 13
<211> LENGTH: 334
<212> TYPE: PRT
<213> ORGANISM: Oryza sativa

<400> SEQUENCE: 13

Met Glu Glu Arg Tyr Glu Ala Leu Lys Glu Leu Gly Ala Gly Asn Phe
1               5                   10                  15

Gly Val Ala Arg Leu Val Arg Asp Lys Arg Ser Lys Glu Leu Val Ala
                20                  25                  30

Val Lys Tyr Ile Glu Arg Gly Lys Lys Ile Asp Glu Asn Val Gln Arg
            35                  40                  45

Glu Ile Ile Asn His Arg Ser Leu Arg His Pro Asn Ile Ile Arg Phe
        50                  55                  60

Lys Glu Val Cys Leu Thr Pro Thr His Leu Ala Ile Val Met Glu Tyr
65                  70                  75                  80

Ala Ala Gly Gly Glu Leu Phe Glu Gln Ile Cys Thr Ala Gly Arg Phe
                85                  90                  95

Ser Glu Asp Asp Ala Arg Tyr Phe Phe Gln Gln Leu Ile Ser Gly Val
                100                 105                 110

Ser Tyr Cys His Ser Leu Glu Ile Cys His Arg Asp Leu Lys Leu Glu
            115                 120                 125

Asn Thr Leu Leu Asp Gly Ser Pro Thr Pro Arg Val Lys Ile Cys Asp
        130                 135                 140

Phe Gly Tyr Ser Lys Ser Ala Leu Leu His Ser Lys Pro Lys Ser Thr
145                 150                 155                 160

Val Gly Thr Pro Ala Tyr Ile Ala Pro Glu Val Leu Ser Arg Lys Glu
                165                 170                 175

Tyr Asp Gly Lys Val Ala Asp Val Trp Ser Cys Gly Val Thr Leu Tyr
            180                 185                 190

Val Met Leu Val Gly Ser Tyr Pro Phe Glu Asp Pro Gly Asp Pro Arg
        195                 200                 205

Asn Phe Arg Lys Thr Ile Ser Arg Ile Leu Gly Val Gln Tyr Ser Ile
    210                 215                 220
```

-continued

Pro Asp Tyr Val Arg Val Ser Ser Asp Cys Arg Arg Leu Leu Ser Gln
225                 230                 235                 240

Ile Phe Val Ala Asp Pro Ser Lys Arg Ile Thr Ile Pro Glu Ile Lys
            245                 250                 255

Lys His Thr Trp Phe Leu Lys Asn Leu Pro Lys Glu Ile Ser Glu Arg
        260                 265                 270

Glu Lys Ala Asp Tyr Lys Asp Thr Asp Ala Ala Pro Pro Thr Gln Ala
            275                 280                 285

Val Glu Glu Ile Met Arg Ile Ile Gln Glu Gly Lys Val Pro Gly Asp
    290                 295                 300

Met Ala Ala Asp Pro Ala Leu Leu Ala Glu Leu Ala Glu Leu Lys
305                 310                 315                 320

Ser Asp Asp Glu Glu Ala Ala Asp Glu Tyr Asp Thr Tyr
                325                 330

<210> SEQ ID NO 14
<211> LENGTH: 342
<212> TYPE: PRT
<213> ORGANISM: Mesembryanthemum crystallinum

<400> SEQUENCE: 14

Met Glu Leu Tyr Glu Ile Val Lys Asp Ile Gly Ser Gly Asn Phe Gly
1               5                   10                  15

Gln Ala Lys Leu Val Arg Asp Lys Trp Thr Asn Glu Phe Val Ala Val
            20                  25                  30

Lys Phe Ile Glu Arg Gly Ser Lys Asp Asp Glu His Val Gln Arg Lys
        35                  40                  45

Leu Met Asn His Ser Ser Leu Lys His Pro Asn Ile Ile Arg Phe Lys
    50                  55                  60

Glu Val Leu Leu Thr Pro Thr His Leu Ala Ile Val Met Glu Tyr Ala
65                  70                  75                  80

Ala Gly Gly Glu Leu Phe Glu Arg Ile Cys Asn Ala Gly Arg Phe Arg
                85                  90                  95

Glu Asp Glu Ala Arg Phe Phe Gln Gln Leu Ile Ser Gly Val Ser
            100                 105                 110

Tyr Cys His Ser Met Gln Ile Cys His Arg Asp Leu Lys Leu Glu Asn
        115                 120                 125

Thr Leu Leu Asp Gly Ser Pro Ala Pro Arg Val Lys Ile Cys Asp Phe
    130                 135                 140

Gly Tyr Ser Lys Ser Ser Val Leu His Ser Gln Pro Lys Ser Ala Val
145                 150                 155                 160

Gly Thr Pro Ala Tyr Ile Ala Pro Glu Val Leu Ser Lys Arg Glu Tyr
                165                 170                 175

Asp Gly Lys Ile Ala Asp Val Trp Ser Cys Gly Val Thr Leu Tyr Val
            180                 185                 190

Met Leu Phe Gly Ala Tyr Pro Phe Glu Asp Pro Asp Pro Lys Asn
        195                 200                 205

Phe Arg Lys Ser Leu Val Arg Ile Leu Ser Val Gln Tyr Cys Ile Pro
    210                 215                 220

Asp Asn Ile Pro Ile Ser Met Glu Cys Arg His Leu Leu Ser Arg Ile
225                 230                 235                 240

Phe Val Ala Asn Pro Glu Lys Arg Ile Thr Ile Pro Glu Ile Lys Asn
                245                 250                 255

His Pro Trp Phe Gln Lys Asn Leu Pro Met Glu Leu Met Glu Gly Gly

```
                260             265             270
Ser Trp Gln Ser His Asp Ile Asn His Pro Ser Gln Asn Ile Gly Glu
            275                 280                 285
Ile Leu Ser Ile Ile Gln Glu Ala Arg Gln Pro Ala Glu Leu Pro Ser
        290                 295                 300
Thr Gly Gly Leu Gln Ile Gly Gly Thr Leu Asp Phe Asp Asp Leu Asp
305                 310                 315                 320
Val Asp Leu Asp Val Asp Val Asp Leu Asp Asp Ile Glu Ser Ser Gly
                325                 330                 335
Glu Phe Val Cys Pro Met
            340

<210> SEQ ID NO 15
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 15

Pro Ile Met His Asp Ser Asp Arg Tyr Asp Phe
1               5                   10

<210> SEQ ID NO 16
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 16

Pro Ala Asp Leu Val Asn Glu Asn Ile Met Asp Asn Gln Phe Glu Glu
1               5                   10                  15

Pro Asp Gln

<210> SEQ ID NO 17
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 17
ttgcyrtyaa rtacatcgaa                                             20

<210> SEQ ID NO 18
<211> LENGTH: 20
<212> TYPE: DNA
<213> ORGANISM: Artificial Sequence
<220> FEATURE:
<223> OTHER INFORMATION: :

<400> SEQUENCE: 18
ccatcyarna gngtrttttc                                             20

<210> SEQ ID NO 19
<211> LENGTH: 30
<212> TYPE: DNA
<213> ORGANISM: Artificial Sequence
<220> FEATURE:
<223> OTHER INFORMATION: :

<400> SEQUENCE: 19
```

```
gaatctccac tacgacgccg tttacttccc                                    30

<210> SEQ ID NO 20
<211> LENGTH: 30
<212> TYPE: DNA
<213> ORGANISM: Artificial Sequence
<220> FEATURE:
<223> OTHER INFORMATION: :

<400> SEQUENCE: 20
ccgtgcaacc atggatatgg catatacaat                                    30
```